(12) United States Patent
Phillips

(10) Patent No.: US 6,811,571 B1
(45) Date of Patent: Nov. 2, 2004

(54) UNIVERSAL PROSTHESIS WITH CUSHIONED ANKLE

(75) Inventor: Van L. Phillips, 5499 Maravillas, P.O. Box 1873, Rancho Santa Fe, CA (US) 92067

(73) Assignees: Van L. Phillips, Albion, CA (US); Ossur HF, Reykjavik (IS)

( * ) Notice: Subject to any disclaimer, the term of this patent is extended or adjusted under 35 U.S.C. 154(b) by 0 days.

(21) Appl. No.: 09/586,666

(22) Filed: Jun. 1, 2000

Related U.S. Application Data

(60) Provisional application No. 60/201,150, filed on May 2, 2000.

(51) Int. Cl.[7] ................................................. A61F 2/66
(52) U.S. Cl. ........................................................ 623/55
(58) Field of Search ............................. 623/47, 49, 53, 623/55

(56) References Cited

U.S. PATENT DOCUMENTS

| | | | |
|---|---|---|---|
| 1,294,632 A | 2/1919 | Dickson | |
| 1,502,593 A | 7/1924 | Shrodes | |
| 2,475,372 A | 7/1949 | Catranis | |
| 3,335,428 A | 8/1967 | Gajdos | |
| 3,874,004 A | 4/1975 | May | |
| 3,940,804 A | 3/1976 | Benton et al. | |
| 4,645,509 A | 2/1987 | Poggi et al. | |
| 4,676,801 A | 6/1987 | Lundeen | |
| 4,865,612 A | 9/1989 | Arbogast et al. | |
| 4,892,553 A | 1/1990 | Prahl | |
| 4,892,554 A | 1/1990 | Robinson | |
| 4,938,776 A | 7/1990 | Masinter | |
| 5,004,477 A | 4/1991 | Palfray | |
| 5,062,859 A | 11/1991 | Naeder | |
| 5,116,381 A | 5/1992 | Palfray | |
| 5,156,632 A * | 10/1992 | Wellershaus | 623/55 |
| 5,181,932 A | 1/1993 | Phillips | |
| 5,181,933 A | 1/1993 | Phillips | |
| 5,219,365 A | 6/1993 | Sabolich | |
| 5,258,038 A | 11/1993 | Robinson et al. | |
| 5,258,039 A | 11/1993 | Goh et al. | |
| 5,290,319 A | 3/1994 | Phillips | |
| 5,376,140 A | 12/1994 | Ryan | |
| 5,443,527 A | 8/1995 | Wilson | |
| 5,443,528 A | 8/1995 | Allen | |
| 5,549,711 A | 8/1996 | Bryant | |
| 5,695,526 A | 12/1997 | Wilson | |
| 5,695,527 A | 12/1997 | Allen | |
| 5,776,205 A * | 7/1998 | Phillips | 623/55 |
| 5,800,569 A | 9/1998 | Phillips | |
| 5,957,981 A * | 9/1999 | Gramnas | 623/47 |
| 5,993,488 A | 11/1999 | Phillips | |
| 6,071,313 A | 6/2000 | Phillips | |
| 6,290,730 B1 * | 9/2001 | Pitkin et al. | 623/49 |

OTHER PUBLICATIONS

Marketplace, Journal of Prosthetics and Orthotics, vol. 8, No. 2, p. 11A, Spring 1996.
Cirrus®, Second Nature Brochure.
SVF–175, Seattle Voyager, Foot/Ankle System, Seattle Limb Systems Brochure.
K2 Sensation™, Flex–Foot Brochure, Jun. 1, 1999.
Footnotes, Flex–Foot Brochure, Summer 1999.

\* cited by examiner

*Primary Examiner*—Bruce E Snow
(74) *Attorney, Agent, or Firm*—Knobbe Martens Olson & Bear, LLP

(57) ABSTRACT

The invention provides a cushioned ankle prosthetic foot and a cosmesis having a slot between the big toe and adjacent toe to allow the amputee to wear thong sandals and the like. The cushioning desirably provides a smooth and more natural-feeling rollover from a heel-strike to a toe-off position and/or improved dynamic response characteristics. Advantageously, the prosthetic foot is configured so that it can be used as either a right or a left foot. Moreover, the cosmesis includes a toe reinforcement strap to desirably provide improved wear resistance to the cosmesis.

50 Claims, 10 Drawing Sheets

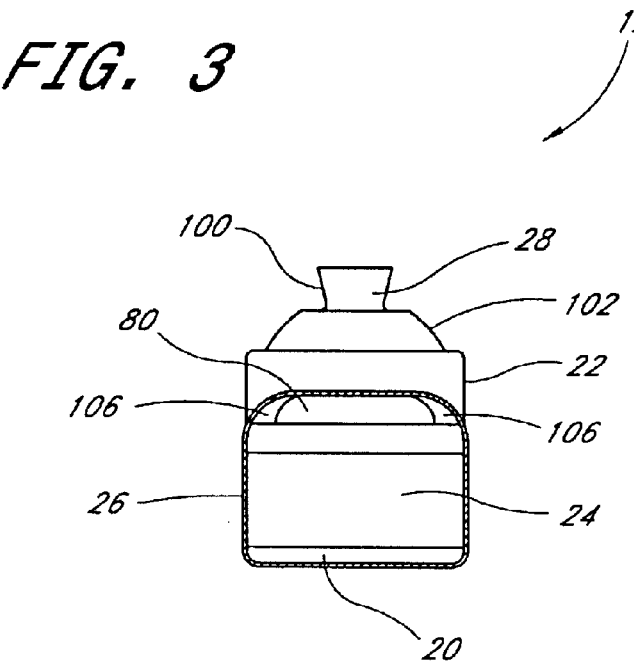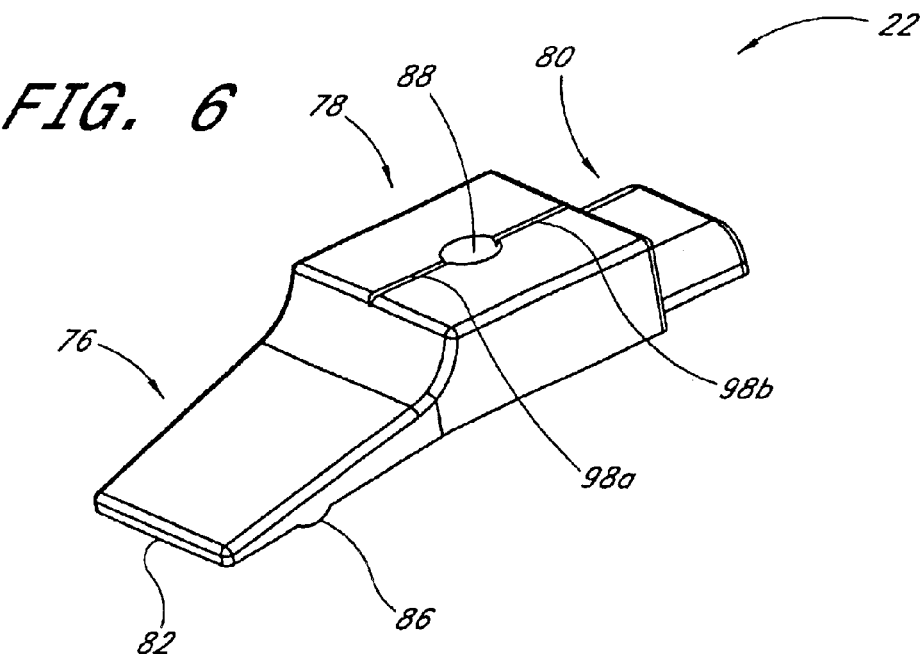

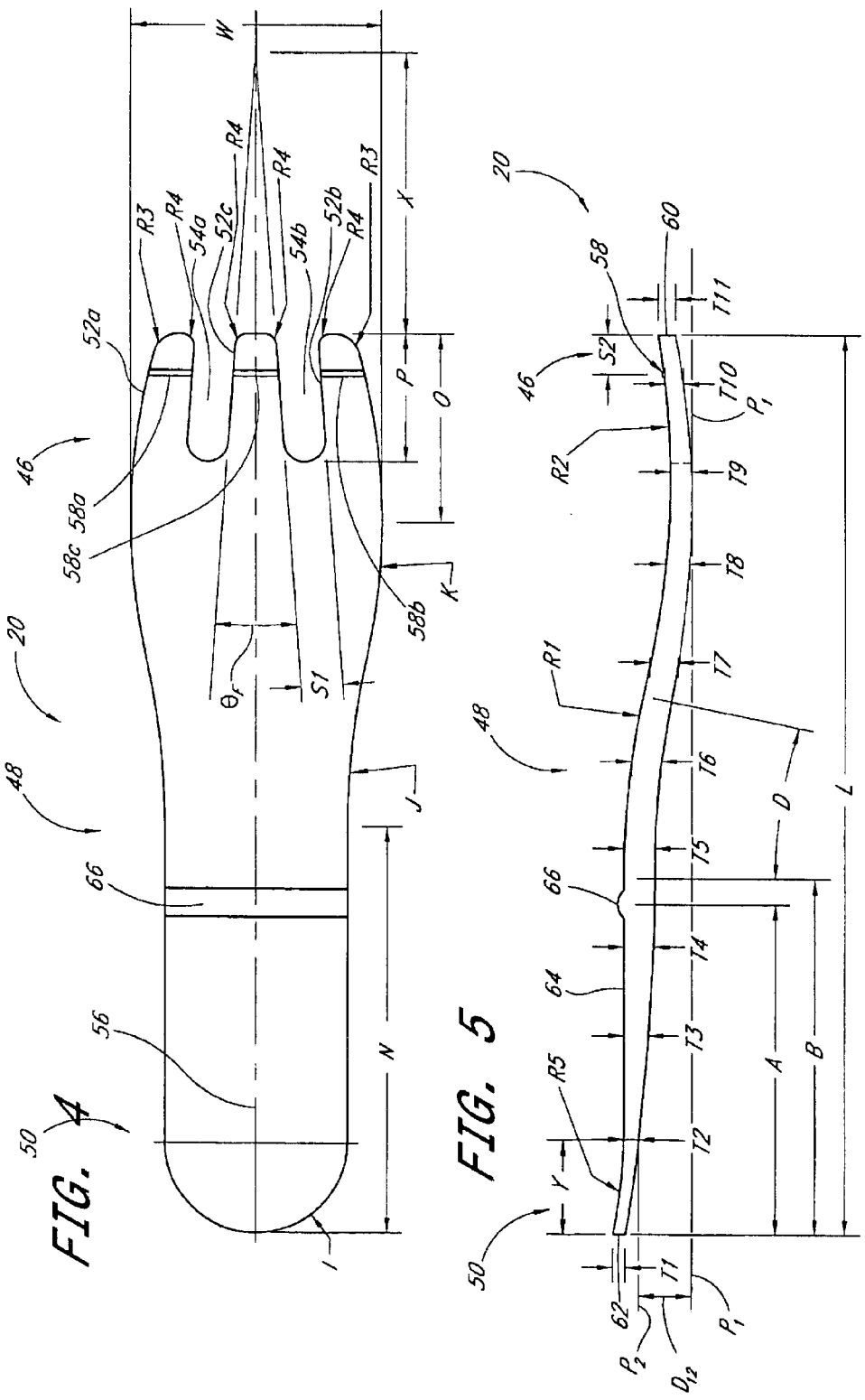

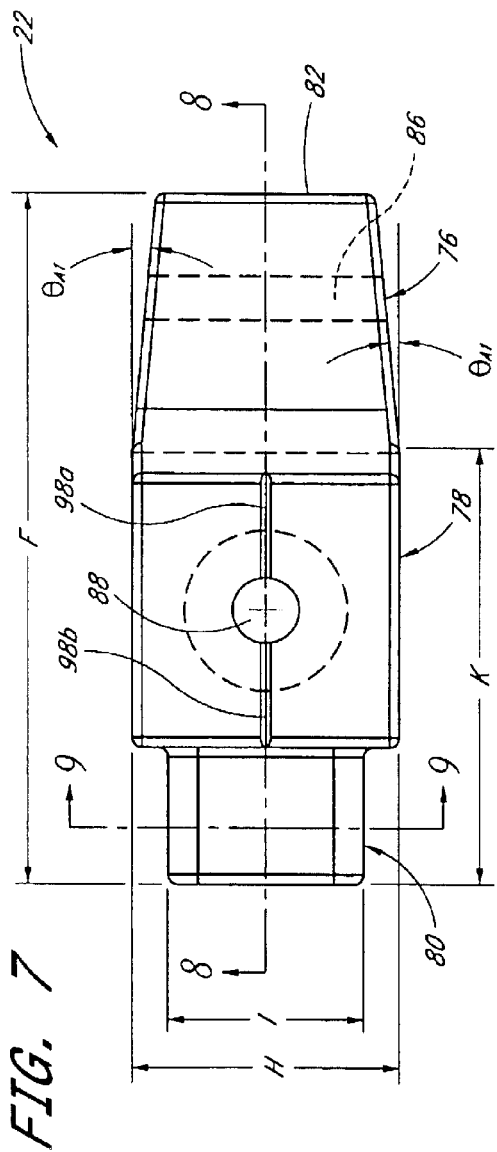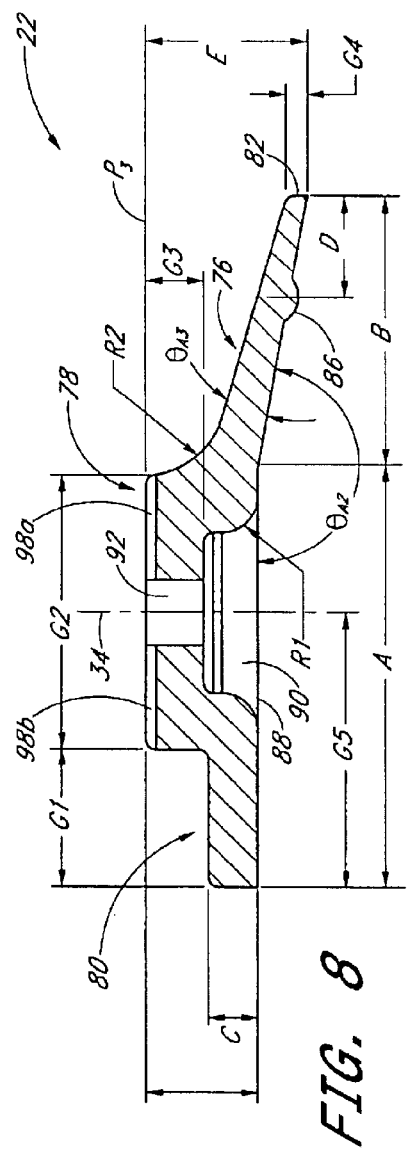

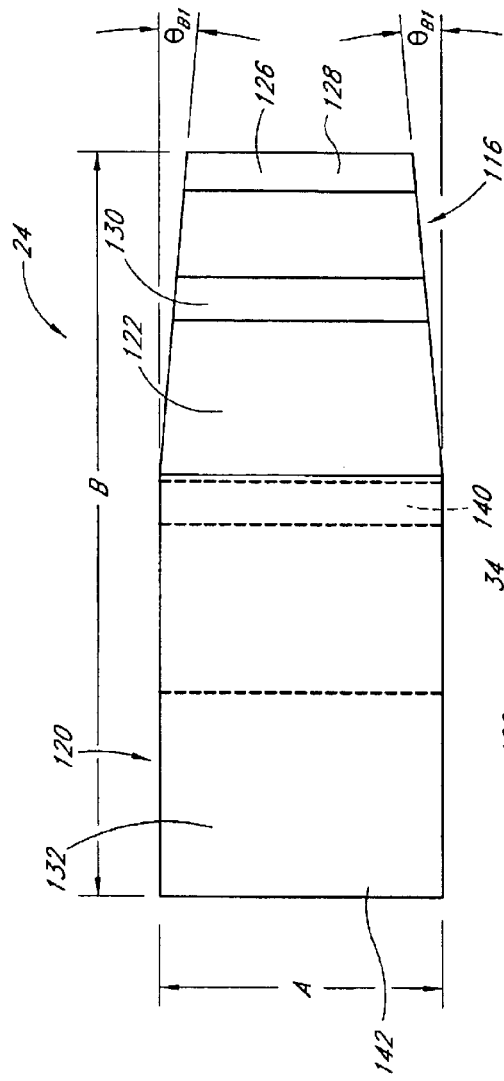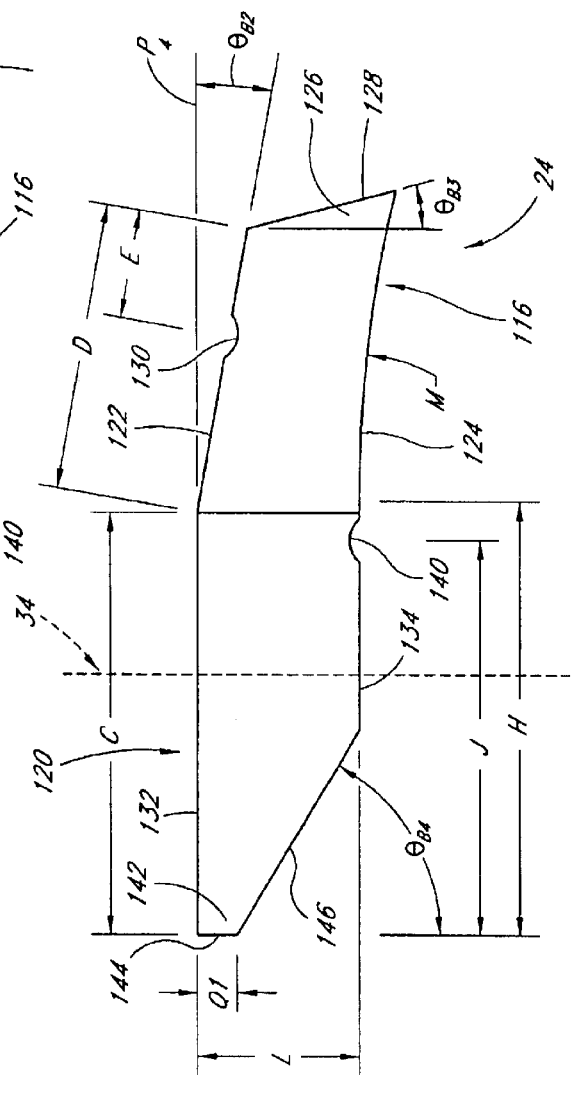
FIG. 11
FIG. 12

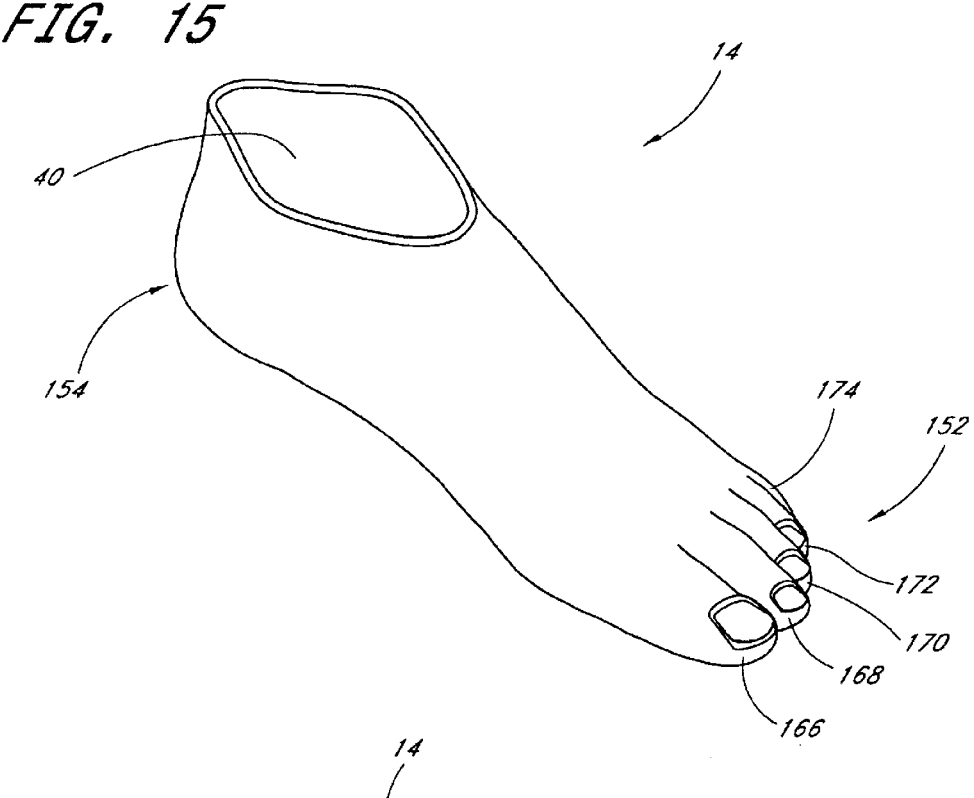
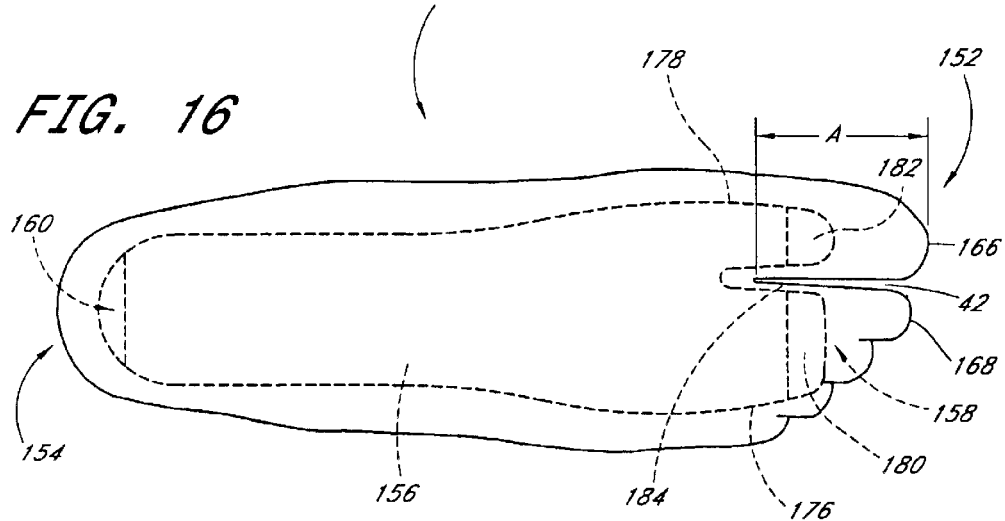

UNIVERSAL PROSTHESIS WITH CUSHIONED ANKLE

Related Applications

This application claims the benefit of U.S. Provisional Application No. 60/201,150, filed May 2, 2000, incorporated herein by reference.

BACKGROUND OF THE INVENTION

1. Filed of the Invention

The present invention relates generally to prosthetic feet and, more particularly, to a prosthetic foot having a cushioned ankle and a thong-receiving reinforced outer foot cosmesis.

2. Description of the Related Art

In the prosthetics market, the conventional SACH foot has been the most widely prescribed artificial foot over the past several decades. The SACH foot generally includes a solid ankle and cushioned heel foot mounted to a limb along an approximate hinge axis taken through the ankle. The SACH foot has been popular precisely for its simplicity, and thus economy, but includes certain drawbacks in terms of dynamic response characteristics. Specifically, the low end SACH feet do not provide much energy storage and release, as do more sophisticated prosthetic feet.

Some patients undergo what is known in the art as a Symes amputation, where the foot is severed from the leg near the ankle region. Because the Symes patient's calf and shin function as the stump for prosthetic purposes, prosthetic devices utilized by the patient must either be relatively compact, so as to be attachable below the point of amputation, or must be configured to accommodate the patient's shin and calf while attached thereto or higher up on the wearer's leg.

Prior art prostheses available to Symes patients typically include an artificial foot bonded or bolted onto the bottom end of a socket worn on a patient's stump. These compact prosthetic feet can also attach below a downwardly depending pylon secured to a socket higher up on the amputee's leg. For such compact prostheses, it is difficult to provide the level of dynamic response approximating the original ankle and foot due to the lack of vertical space available.

Some attempts at providing the appropriate response characteristics of the original ankle and foot in Symes foot prosthesis involve the use of rubber cushions, or bumpers, between a lower leg and the foot. Many of these require a pivotable bolt attachment between the leg and the foot. Unfortunately, many of these rubber cushion devices have limited durability due to the difficulty in bonding the rubber portions to the solid leg or foot portions, or are relatively complex, requiring several machined parts, which adds to the cost.

U.S. Pat. Nos. 5,800,569 and 5,993,488, incorporated by reference herein, to Phillips disclose a resilient ankle block prosthesis that mitigates or overcomes some of the above disadvantages. But, there is still room for further improvements in providing a smooth and more natural-feeling rollover from a heel-strike to a toe-off position and/or of providing improved dynamic response characteristics, so as to provide a natural feeling foot during walking or running activities.

There are also a number of foot cosmesis that are presently commercially available in the market. The cosmesis for an artificial foot serves as a cosmetic outer cover and provides the appearance of a relatively natural looking foot for the lower limb amputee.

Conventional artificial feet and/or cosmesis can disadvantageously also be limited in terms of the flexibility and versatility they provide in allowing the amputee to don different types of conventional footwear. Moreover, the frictional contact between the artificial foot and the cosmesis can cause wear of the cosmesis, especially at the high stress contact points. This can not only result in inconvenient frequent replacement of the cosmesis but also further adds to the cost for the amputee. Additionally, many artificial feet are adapted to be used only as a left or right foot and not both, and this undesirably limits versatility and increases manufacturing and inventory costs.

Consequently, there is a need for a relatively inexpensive, durable and versatile prosthetic foot assembly with improved performance characteristics.

SUMMARY OF THE INVENTION

Accordingly, it is one object and advantage of the present invention to overcome some or all of the above limitations by providing a cushioned ankle prosthetic foot and an associated cosmesis having a slot between the big toe and adjacent toe to allow the amputee to wear thong sandals and the like. The cushioning desirably provides a smooth and more natural-feeling rollover from a heel-strike to a toe-off position and/or improved dynamic response characteristics. Advantageously, the prosthetic foot is configured so that it can be used as either a right or a left foot. Moreover, the cosmesis includes a toe reinforcement strap to desirably provide improved wear resistance to the cosmesis.

In accordance with one preferred embodiment of the invention, a prosthetic foot assembly for a lower limb amputee is provided. The assembly generally comprises a prosthetic foot and an outer cosmesis. The prosthetic foot attaches to a socket or pylon of the lower limb amputee. The prosthetic foot generally comprises a lower foot plate and an upper ankle plate. The lower foot plate includes a symmetric toe configuration and a plurality of slots formed therebetween. The upper ankle plate has a length substantially shorter than the foot plate. The prosthetic foot further comprises an ankle block having a wedged configuration. The ankle block comprises a compressible material and is sandwiched between the foot plate and the ankle plate. The outer cosmesis has a length approximately equal to the length of a natural human foot and has an anterior toe region including a slot substantially aligned with one of the slots of the foot plate. Advantageously, the prosthetic foot assembly permits the lower limb amputee to wear thong sandals and the like and/or provides enhanced performance characteristics.

In accordance with another preferred embodiment of the invention, an outer foot cosmesis is provided. The outer foot cosmesis has a length substantially the same as that of a natural human foot. The cosmesis comprises an inner cavity for receiving a prosthetic foot for attaching to a socket or pylon of a lower limb amputee. The cosmesis has a toe portion comprising at least one slot for receiving a thong of a sandal or other footwear. The cosmesis further comprises a reinforcement patch in the toe portion for improving the wear resistance of the cosmesis.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 3 is a simplified rear view of the prosthetic foot of FIG. 1.

FIG. 4 is a top plan view of a lower foot plate of the prosthetic foot assembly of FIG. 1 having features in accordance with one preferred embodiment of the present invention.

FIG. 5 is a side elevation view of the lower foot plate of FIG. 4.

FIG. 6 is a perspective view of an upper ankle plate of the prosthetic foot assembly of FIG. 1 having features in accordance with one preferred embodiment of the present invention.

FIG. 7 is a top plan view of the upper ankle plate of FIG. 6.

FIG. 8 is a sectional view along line 8—8 of FIG. 7.

FIG. 11 is a top plan view of the compressible ankle block of FIG. 10.

FIG. 12 is a side elevation view of the compressible ankle block of FIG. 10.

FIG. 15 is a perspective view of the outer cosmesis of FIG. 13.

FIG. 16 is a bottom plan view (showing some hidden lines) of the outer cosmesis of FIG. 13.

DETAILED DESCRIPTION OF THE PREFERRED EMBODIMENTS

Figure 1:
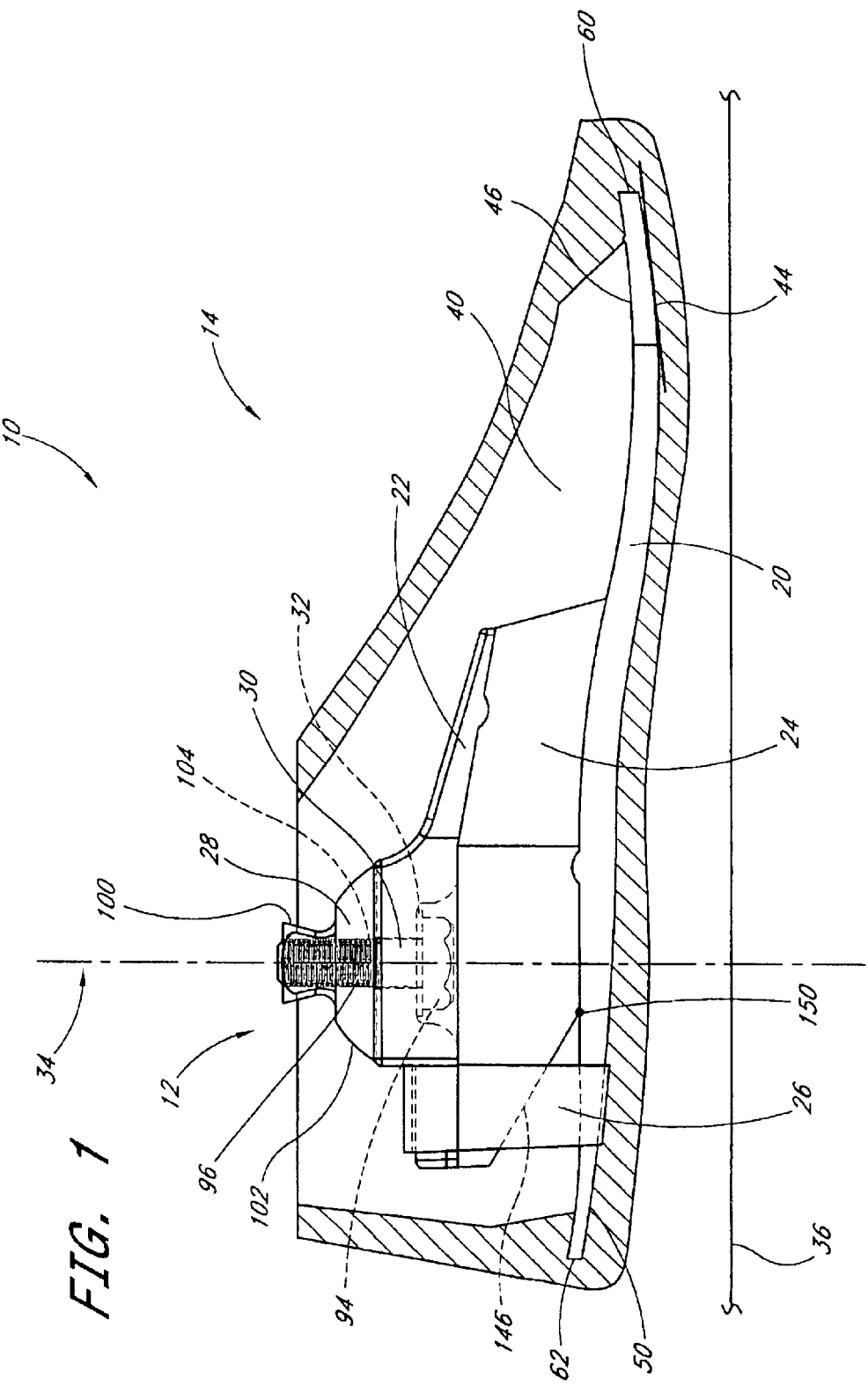
FIG. 1 is a simplified partially sectional side elevation view of a prosthetic foot assembly having features in accordance with one preferred embodiment of the present invention.
Figure 2:
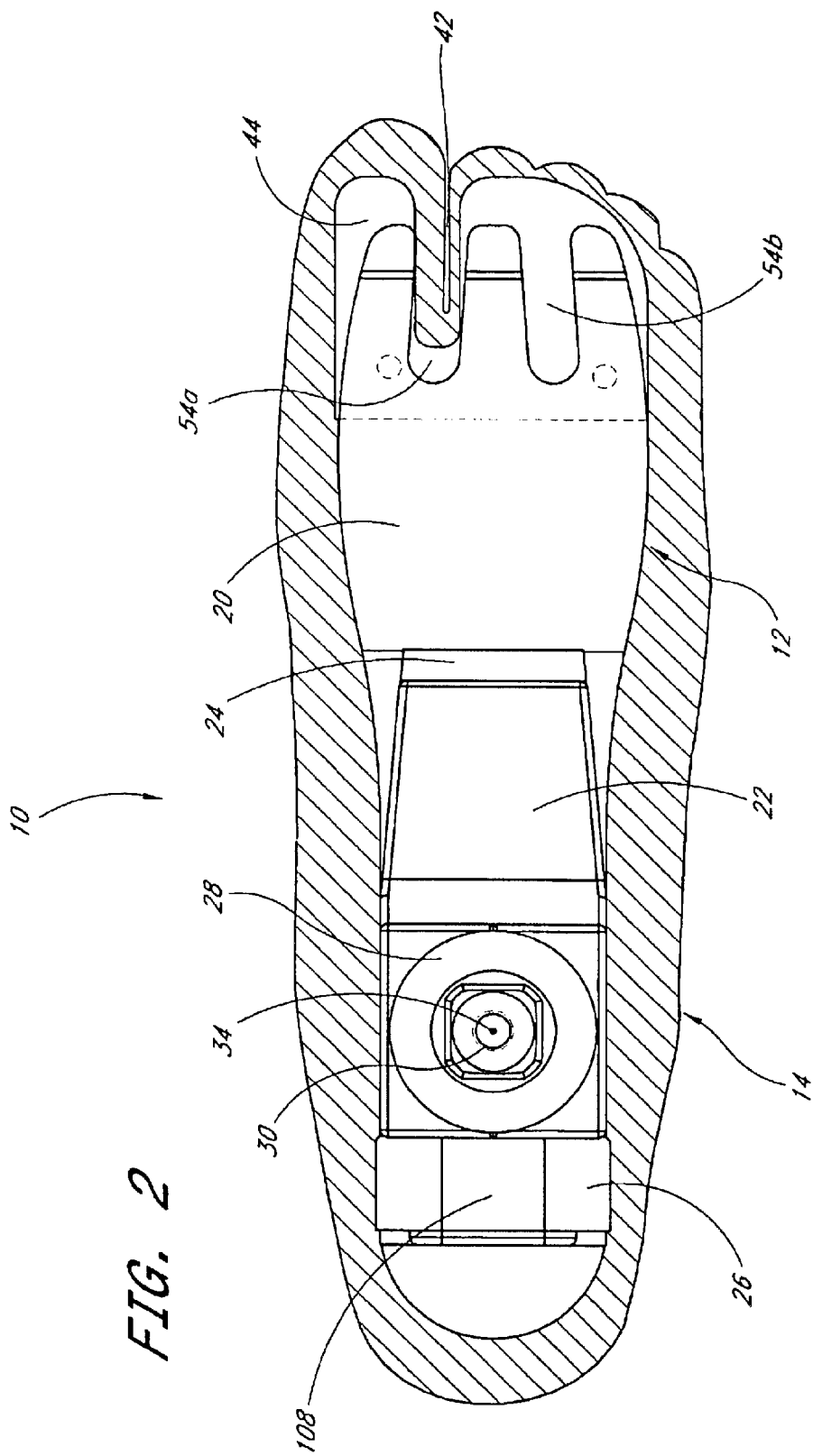
FIG. 2 is a simplified partially sectional top plan view of the prosthetic foot assembly of FIG. 1.
Figure 9:
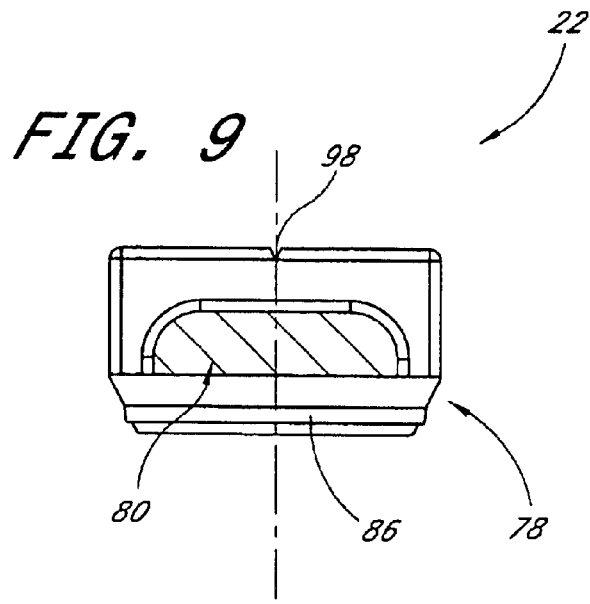
FIG. 9 is a sectional view along line 9—9 of FIG. 7.
Figure 10:
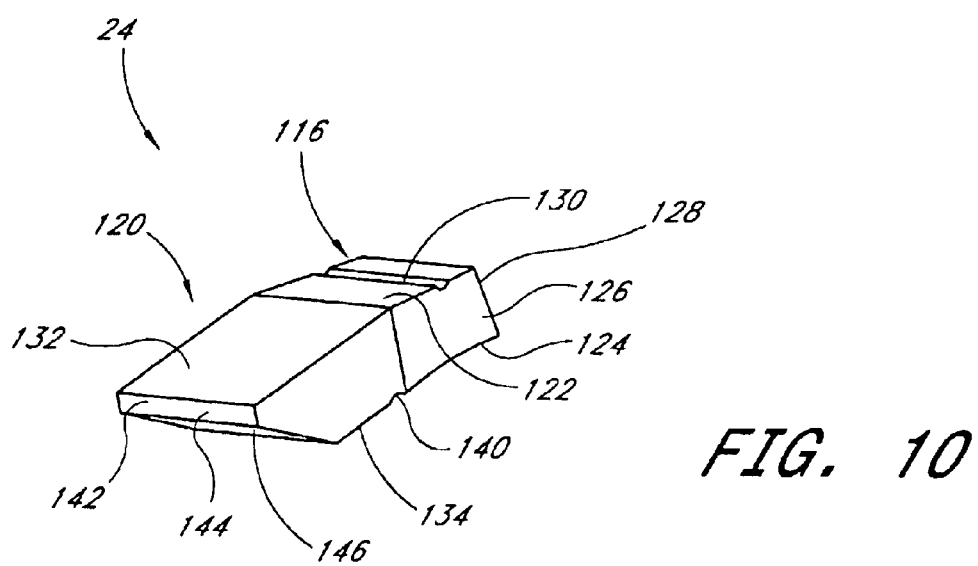
FIG. 10 is a perspective view of a compressible ankle block of the prosthetic foot assembly of FIG. 1 having features in accordance with one preferred embodiment of the present invention.
Figure 14:
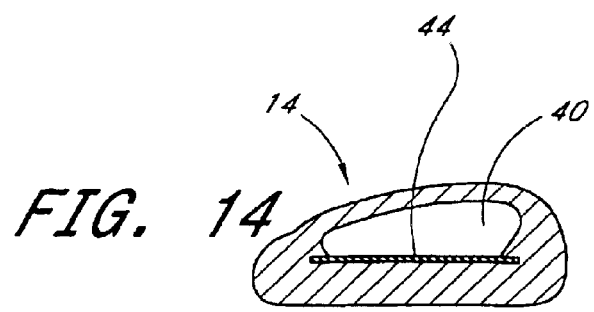
FIG. 14 is a sectional view along line 14—14 of FIG. 13.

FIGS. 1 and 2 illustrate a prosthetic or artificial foot assembly or combination 10 having features in accordance with one preferred embodiment of the present invention. The prosthetic foot assembly or foot prosthesis 10 generally comprises a prosthetic or artificial foot 12 and an outer foot cover or cosmesis 14. For clarity, a sectional illustration of the cosmesis 14 is shown in FIGS. 1 and 2. FIG. 3 is a rear view of the prosthetic foot 12.

The prosthetic foot or prosthesis 12 generally comprises a lower foot plate 20, an upper, smaller ankle plate 22, and a layer or block 24 of resilient material sandwiched between and connecting the foot plate 20 to the ankle plate 22. In one preferred embodiment, the lower foot plate 20 comprises a symmetric toe configuration, thereby desirably permitting the prosthetic foot 12 to be used as either a left or right foot. Advantageously, this saves on manufacturing and inventory costs.

Preferably, and as discussed in greater detail below, the intermediate ankle block 24 is bonded to the foot plate 20 and ankle plate 22. Preferably, and as also discussed in greater detail below, the foot plate 20 and the ankle plate 22 comprise a strong, flexible material. Advantageously, during a walking and/or running stride, the combination of the resilient ankle block or keel 24 and the flexible plates 20, 22 provides a smooth rollover from a heel-strike to a toe-off position.

In one preferred embodiment, a limit strap 26 is used to further secure the foot plate 20, the ankle block 24 and the ankle plate 22. The limit strap 26 controls or limits the maximum degree of displacement (expansion) of the ankle block 24 and the relative motion between the foot plate 20 and the ankle plate 22 proximate the heel portion of the prosthesis 12.

Preferably, the ankle or connector plate 22 is coupled to an attachment member 28 for coupling the prosthetic foot 12 to a downwardly depending leg such as a stump or lower-limb pylon of the amputee or wearer. The ankle plate 22 is preferably connected to the attachment member 28 utilizing a bolt 30 and a washer 32. The center or longitudinal axis of the bolt 30 defines an attachment axis 34 which is generally aligned with the vertical centerline of an imaginary ankle so as to more faithfully simulate the location at which forces are transmitted between leg and foot.

The cosmesis or foot cover 14 is generally shaped, sized and/or configured to generally emulate the appearance of a natural human foot. The cosmesis 14 is preferably constructed of a resilient material. Preferably, the cosmesis 14 comprises an inner cavity 40 shaped, sized and/or configured to receive the prosthetic foot 12.

In one preferred embodiment, the cosmesis 14 comprises a slit or slot 42 (FIG. 2) in the toe region to receive a thong or the like of a thong sandal or other footwear. Desirably, this adds to the versatility of the invention. The cosmesis 14 preferably further comprises a reinforcement patch or strap 44 in or near the toe region to provide durability.

A supporting ground or floor surface 36 is also shown in FIG. 1. The spacing or gap between the cosmesis 14 (or prosthetic foot assembly 10) and the surface 36 and the orientation of the cosmesis 14 relative to the surface 36 are indicative of an intermediate sole and/or heel of a shoe or other footwear worn by the amputee. Those of ordinary skill in the art will recognize that when the amputee is not wearing a shoe or other footwear, the cosmesis 14 can be in direct contact with the ground or floor surface 36.

As is known in the art, see for example U.S. Pat. Nos. 5,800,569 and 5,993,488, incorporated by reference herein, ambulation comprises several foot positions with respect to a supporting ground or floor surface. The several walking and/or running strides include a heel-strike position, a generally flat-foot position, a heel-off position and a toe-off position. Throughout these various stride positions, the prosthetic foot 12 of the invention advantageously provides a smooth and generally life-like response to the wearer. During a walking and/or running stride, the ankle block 24 transmits the forces imparted thereon by the foot plate 20 and the ankle plate 22, and experiences a gradual rollover, or migration of the compressed region, from rear to front.

Lower Foot Plate

In one preferred embodiment, and referring in particular to FIGS. 4 and 5, the lower or bottom foot plate or member 20 generally comprises an anterior toe region or portion 46, a medial arch region or portion 48 and a posterior heel region or portion 50. Preferably, the foot plate 20 has a curvilinear shape (FIG. 4), including a slight arch in the center section 48 and a slightly upwardly curved toe section 46 and heel section 50. Desirably, this generally simulates the natural curve of the sole of a human foot.

The curvature(s) of the lower surface of the foot plate 20 generally corresponds to the profile of an associated contacting surface of the cosmesis 14 and/or to the profile of an associated shoe sole. The curvature(s) of the upper surface of the foot plate 20 generally corresponds to selected ranges of human lengths. Optionally, the foot plate 20 can comprise a generally flat plate, as needed or desired.

Preferably, the foot plate 20 has a thickness along its length that is tapered, and the tapered profile corresponds approximately to the weight of the amputee. That is, for a heavier weight group amputee, the thickness along the length of the foot plate 20 would be generally greater than that for a lighter weight group amputee.

The foot plate 20 preferably has a length and width roughly equal to or slightly smaller than the approximate length and width of the particular wearer's amputated foot and is sized, shaped and/or configured to fit within the outer flexible cosmesis 14. Preferably, and as shown in FIG. 4, the width of the foot plate 20 is greater towards the front and follows a curved profile to define a maximum width (W) at or near the junction between the toe region 46 and the arch region 48. Desirably, this simulates the approximate shape or contour of a natural foot. Optionally, foot plate 20 may include a lower sole cushion to provide protection to the inner surfaces of the cosmesis 14.

In other preferred embodiments, the foot plate 20 can be shaped, sized and/or configured in alternate manners with efficacy, as required or desired, giving due consideration to the goals of providing a suitably strong and generally natural feeling prosthetic foot, and/or of achieving one or more of the advantages and benefits as taught or suggested herein.

The lower foot plate 20 is preferably capable of flexing along its length. Desirably, the flexing of the foot plate 20 under the weight of the amputee tends to distribute and/or relieve shear stresses applied at the interface between the foot plate 20 and ankle block 24. Moreover, the flexing contributes to a more natural feeling walking and/or running stride for the wearer of the prosthetic foot 12.

In one preferred embodiment, the toe or front section 46 of the foot plate 20 comprises a plurality of generally elongated spaced toes 52. Most preferably, the toe section 46 comprises three toes 52 (labeled 52a, 52b, 52c) and two corresponding slots 54 (labeled 54a, 54b) formed therebetween. In other preferred embodiments, the toe section 46 can efficaciously comprise fewer or more toes, as required or desired, giving due consideration to the goals of achieving one or more of the advantages and benefits as taught or suggested herein. Optionally, the toe section 46 may not be slotted to form individual toes and/or the foot plate 20 may comprise a generally flat plate, as needed or desired.

In one preferred embodiment, the toes 52a, 52b, 52c (and hence the slots 54a, 54b) are arranged to form a generally symmetric configuration about a longitudinal axis 56 of the foot plate 20. Desirably, this allows the foot plate 20 to be used as part of a left or right prosthetic foot 12. In other preferred embodiments, the toes 52 and slots 54 can be efficaciously arranged in alternate configurations, as required or desired, giving due consideration to the goals of achieving one or more of the advantages and benefits as taught or suggested herein.

The slots 54 (and toes 52) are sized, shaped and/or configured so that when the foot plate 20 is seated in the cosmesis 14, a respective one of the slots 54a, 54b is substantially aligned with the thong-receiving slot 42 (FIG. 2). The particular toe slot 54a or 54b that is aligned with the cosmesis slot 42 (and a corresponding slot of the reinforcement patch 44) depends on whether the cosmesis 14 is a right or left foot cosmesis. For illustration purposes, a right foot cosmesis 14 is shown in FIG. 2 in which the toe slot 54a is aligned with the cosmesis slot 42, though the skilled artisan will realize that a left foot cosmesis is substantially a mirror image of a right foot cosmesis in which the toe slot 54b will be aligned with the corresponding cosmesis slot.

Advantageously, the symmetric toe configuration of the foot plate 20 allows the prosthetic foot 12 to be readily used in conjunction with a cosmesis 14 of a right or left foot. Desirably, this saves on manufacturing and inventory costs, and also adds to the versatility of the invention.

Preferably, the outer toes 52a, 52b are slightly inwardly curved towards the foot plate longitudinal axis 56 and the center or middle toe 52c is substantially aligned with the longitudinal axis 56. In other preferred embodiments, the toes 52 and slots 54 can be efficaciously arranged in alternate configurations, as required or desired, giving due consideration to the goals of achieving one or more of the advantages and benefits as taught or suggested herein.

Each one of the toes 52 preferably includes a marker 58 (labeled 58a, 58b, 58c in FIG. 4) in the form of a slightly raised crosswise portion, rib or bump on each of the upper surfaces of the toes 52. As discussed below, the location of the markers 58 generally corresponds to a smaller foot size. This allows the portion of the toes 52 extending beyond the bumps 58 to be trimmed down to form a foot plate 20 for a smaller or intermediate foot size. Advantageously, this saves on manufacturing and inventory costs.

In another preferred embodiment, the markers or indicators 58 can comprise grooves. In yet another preferred embodiment, the markers 58 comprise bands which are colored to provide visual differentiation. In other preferred embodiments, as the skilled artisan will recognize, the markers 58 can be alternately formed and/or constructed with efficacy, as required or desired, giving due consideration to the goals of providing size indicating means, and/or of achieving one or more of the advantages and benefits as taught or suggested herein.

The toe portion 46 has a toe end 60 and is preferably slightly uplifted or generally concave-upward relative to a generally horizontal plane $P_1$ tangential to the toe section 46, as shown in FIG. 5. As indicated before, the curvature of the toe portion 46 generally simulates the natural curve of the toe region of the sole of a human foot. In other preferred embodiments, the toe region 46 can be efficaciously configured in alternate manners, as required or desired, giving due consideration to the goals of providing a generally natural feeling prosthetic foot 12, and/or of achieving one or more of the advantages and benefits as taught or suggested herein.

The heel or rear section or portion 50 has a heel end 62 and is preferably slightly uplifted or generally concave-upward relative to a generally horizontal plane $P_2$. The plane $P_2$ is substantially parallel to and slightly raised, offset or elevated by a predetermined distance ($D_{12}$) relative to the plane $P_1$. As indicated before, the curvature of the heel portion 50 generally simulates the natural curve of the heel region of the sole of a human foot. In other preferred embodiments, the heel region 50 can be efficaciously configured in alternate manners, as required or desired, giving due consideration to the goals of providing a generally natural feeling prosthetic foot 12, and/or of achieving one or more of the advantages and benefits as taught or suggested herein.

It is understood that within the cosmesis 14 (FIG. 1), the heel plane $P_2$ is raised by a distance $D_{12}$ relative to the toe plane $P_1$. The magnitude of $D_{12}$ is largely determined by the particular configuration of the cosmesis 14 and/or that of the sole and heel of the shoe or other footwear donned by the wearer. For example, for a higher shoe heel the distance $D_{12}$ will be larger as compared to for a shorter shoe heel.

The central or middle arch section 48 is intermediate or between the toe section 46 and the heel section 50 and is preferably generally concave downward. As indicated before, the curvature of the arch portion 48 generally simulates the natural curve of the arch region of the sole of a human foot. The regions of the arch section 48 proximate to the toe section 46 and heel section 50 can be slightly concave upward. In other preferred embodiments, the central region 48 can be efficaciously configured in alternate manners, as required or desired, giving due consideration to the goals of providing a generally natural feeling prosthetic foot 12, and/or of achieving one or more of the advantages and benefits as taught or suggested herein.

In one preferred embodiment, the arch section 48 comprises a substantially flat upper surface 64 adjacent to the heel section 50. In other preferred embodiments, the central region 48 can be efficaciously configured in alternate manners, as required or desired, giving due consideration to the goals of providing a generally natural feeling prosthetic foot 12, and/or of achieving one or more of the advantages and benefits as taught or suggested herein.

In general or on the average, the arch section 48 of the foot plate 20 is thicker than the other sections of the foot plate 20. In other preferred embodiments, the central arch region 48 can be efficaciously dimensioned in alternate manners, as required or desired, giving due consideration to the goals of providing a generally natural feeling prosthetic foot 12, and/or of achieving one or more of the advantages and benefits as taught or suggested herein.

In one preferred embodiment, the upper surface of the arch section 48 comprises a location rib or bump 66 for establishing the relative positioning between the foot plate 20 and the ankle block 24. The location bump 66 mates with or engages a corresponding groove on the lower surface of the ankle block 24. The rib 66 may also provide added protection against separation, peeling or delamination between the foot plate 20 and the ankle block 24.

Alternatively, the location rib may be provided on the ankle block 24 and the corresponding groove may be provided on the foot plate 20. Additionally, other positioning means such as location pins and the like may be efficaciously used, as required or desired, giving due consideration to the goals of establishing the desired positioning between the foot plate 20 and the ankle block 24, and/or of achieving one or more of the advantages and benefits as taught or suggested herein.

Preferably, the location rib 66 extends crosswise across the span of the upper surface of the foot plate 20. In other preferred embodiments, the rib 66 (and corresponding groove) can be positioned and configured in alternate manners with efficacy, as required or desired, giving due consideration to the goals of establishing the desired positioning between the foot plate 20 and the ankle block 24, and/or of achieving one or more of the advantages and benefits as taught or suggested herein.

Preferably, the foot plate 20 is fabricated from a vinyl ester based sheet molding compound, such as Quantum QC-8800, available from Quantum Composites of Midland, Mich. The foot plate 20 preferably comprises a vinyl ester resin matrix with a substantially randomly arranged fiberglass fiber content. In another preferred embodiment, the foot plate 20 is constructed of fiberglass. Alternatively, the foot plate 20 may be formed by a plurality of lamina embedded in a hardened flexible polymer. The foot plate 20 can also be formed of carbon fibers.

In other arrangements, the foot plate 20 may be formed of alternate suitable materials, such as other composite materials, plastics, thermoplastic and thermosetting polymers, metals, alloys and ceramics among others, as required or desired, giving due consideration to the goals of achieving one or more of the advantages and benefits as taught or suggested herein. The desirable properties of the foot plate 20 are that it is relatively resilient so as to withstand cracking upon application of repeated bending stresses, yet has sufficient flexibility to enhance the performance characteristics felt by the wearer, in conjunction with the properties of the resilient ankle block 24 and the ankle plate 22.

Preferably, the foot plate 20 is formed by a molding process. More preferably, the foot plate 20 is formed by a compression molding process. Alternatively, the foot plate 20 can be formed by an injection molding process. In other preferred embodiments, the foot plate 20 can be fabricated using other techniques, for example, machining, welding, laminating, casting and forging among others, with efficacy, as required or desired, giving due consideration to the goals of providing enhanced performance, and/or of achieving one or more of the advantages and benefits as taught or suggested herein.

TABLES 1A–1B below, in accordance with one preferred embodiment, list various approximate dimensions of the foot plate 20 for various amputee foot and weight sizes. The number and letter in the "SIZE" column in TABLES 1A–1B respectively refer to the cosmesis size or overall length in centimeters and the weight group (L=Light, M=Medium, H=Heavy) of the amputee. The other column heading symbols in TABLES 1A–1B refer to dimensional labels as marked on FIGS. 4–5. T1 to T11 refer to thicknesses (in inches), A, B, L, N, 0, P, X, Y refer to length scales (in inches), W refers to a width (in inches), R1, R2, R3, I, J, K refer to radii of curvature (in inches) and D refers to an angle in degrees (°). Note that the thicknesses T1 to T11 are taken at positions spaced by the corresponding value of Y, that is, the position at which T1 is taken is spaced from the position where T2 is taken by Y, and so on. It will be appreciated that other dimensions than those of TABLES 1A–1B may be used, as needed or desired.

TABLE 1A

FOOT PLATE DIMENSIONS FOR DIFFERENT AMPUTEE SIZES (CORRESPONDS TO FIGS. 4 AND 5)

| SIZE | A | B | D | R1 | R2 | R3 | I | J | K | L | N | O | P |
|---|---|---|---|---|---|---|---|---|---|---|---|---|---|
| 22L | 2.75 | 3.00 | 18.0° | 5.75 | 5.75 | .19 | .75 | 6.50 | 5.25 | 7.27 | 3.250 | 1.423 | .94 |
| 22H | 2.75 | 3.00 | 18.0° | 5.75 | 5.75 | .19 | .75 | 6.50 | 5.25 | 7.27 | 3.250 | 1.423 | .94 |
| 24L | 3.00 | 3.25 | 16.0° | 7.00 | 7.00 | .19 | .82 | 7.00 | 5.75 | 8.06 | 3.640 | 1.650 | 1.10 |
| 24M | 3.00 | 3.25 | 16.0° | 7.00 | 7.00 | .19 | .82 | 7.00 | 5.75 | 8.06 | 3.640 | 1.650 | 1.10 |
| 24H | 3.00 | 3.25 | 16.0° | 7.00 | 7.00 | .19 | .82 | 7.00 | 5.75 | 8.06 | 3.640 | 1.650 | 1.10 |
| 26L | 3.25 | 3.50 | 13.0° | 8.75 | 8.75 | .25 | .88 | 7.63 | 6.25 | 8.85 | 4.000 | 1.860 | 1.26 |
| 26M | 3.25 | 3.50 | 13.0° | 8.75 | 8.75 | .25 | .88 | 7.63 | 6.25 | 8.85 | 4.000 | 1.860 | 1.26 |
| 26H | 3.25 | 3.50 | 13.0° | 8.75 | 8.75 | .25 | .88 | 7.63 | 6.25 | 8.85 | 4.000 | 1.860 | 1.26 |
| 28L | 3.50 | 3.75 | 13.5° | 9.50 | 9.50 | .25 | .95 | 8.25 | 6.77 | 9.60 | 4.398 | 1.981 | 1.50 |
| 28H | 3.50 | 3.75 | 13.5° | 9.50 | 9.50 | .25 | .95 | 8.25 | 6.77 | 9.60 | 4.398 | 1.981 | 1.50 |

TABLE 1B

FOOT PLATE DIMENSIONS FOR DIFFERENT AMPUTEE SIZES (CORRESPONDS TO FIGS. 4 AND 5)

| SIZE | W | X | Y | T1 | T2 | T3 | T4 | T5 | T6 | T7 | T8 | T9 | T10 | T11 |
|---|---|---|---|---|---|---|---|---|---|---|---|---|---|---|
| 22L | 2.082 | 2.60 | .79 | .064 | .089 | .169 | .224 | .233 | .221 | .207 | .170 | .146 | .117 | .107 |
| 22H | 2.082 | 2.60 | .79 | .078 | .103 | .183 | .238 | .247 | .235 | .221 | .184 | .160 | .131 | .121 |
| 24L | 2.250 | 2.70 | .86 | .066 | .092 | .175 | .232 | .241 | .228 | .214 | .176 | .151 | .121 | .111 |
| 24M | 2.250 | 2.70 | .86 | .080 | .106 | .189 | .246 | .255 | .242 | .228 | .190 | .165 | .135 | .125 |
| 24H | 2.250 | 2.70 | .86 | .095 | .121 | .204 | .261 | .270 | .257 | .243 | .205 | .180 | .150 | .140 |
| 26L | 2.417 | 2.75 | .93 | .083 | .109 | .195 | .253 | .262 | .249 | .235 | .196 | .170 | .139 | .129 |
| 26M | 2.417 | 2.75 | .93 | .098 | .124 | .210 | .268 | .277 | .264 | .250 | .211 | .185 | .154 | .144 |
| 26H | 2.417 | 2.75 | .93 | .119 | .145 | .231 | .289 | .298 | .285 | .271 | .232 | .206 | .175 | .165 |
| 28L | 2.600 | 2.60 | 1.00 | .101 | .127 | .216 | .275 | .285 | .271 | .257 | .217 | .190 | .158 | .148 |
| 28H | 2.600 | 2.60 | 1.00 | .122 | .148 | .237 | .296 | .306 | .292 | .278 | .238 | .211 | .179 | .169 |

TABLE 2 below lists intermediate amputee foot sizes which can utilize foot plates 20 which are trimmed down from the standard sizes of TABLES 1A–1B. As discussed above, markers 58 which are already formed on the foot plate toes 52 facilitate this trim-down process. Advantageously, such a scheme saves on manufacturing and inventory costs.

TABLE 2

FOOT PLATE INTERMEDIATE TRIM DOWN SIZES

| SIZE | TRIM DOWN FROM FOOT PLATE FOR SIZE |
|---|---|
| 21L | 22L |
| 21H | 22H |
| 23L | 24L |
| 23M | 24M |
| 23H | 24H |
| 25L | 26L |
| 25M | 26M |
| 25H | 26H |
| 27L | 28L |
| 27H | 28H |

In one preferred embodiment, and referring to FIGS. 4 and 5, the distance S1 is about 0.40 inches, the radii of curvature R4 are about 0.12 inches, the angle $\theta_F$ is about 8°, R5 is about 5 inches, the distance S2 is about 0.39 inches, the marker bump 58 has a radius of curvature of about 0.03 inches and a height of about 0.015 inches, the location rib 66 has a radius of curvature of about 0.19 inches and a height of about 0.06 inches, and the radius of curvature at the peripheral edge of the lower surface of the foot plate 20 is about 0.06 inches. The foot plate 20 may be otherwise dimensioned, as needed or desired.

Upper Ankle Plate

Referring to the drawings, and in particular to FIGS. 1–3 and 6–9, the upper ankle plate or member 22 is smaller in length than the foot plate 20 and has average and major widths smaller than the respective average and major widths of the foot plate 20. The ankle plate 22 is preferably centered transversely with respect to the foot plate 20. Preferably, the ankle plate 22 is generally positioned over the back portion of the arch section 48 of the lower foot plate 20 and substantially above the ankle block 24. The ankle plate 22 preferably extends substantially more forward of the attachment axis 34 (FIG. 1) than rearwardly. The contour of the lower surface of the ankle plate generally conforms to the contour of the upper surface of the ankle block 24.

In other preferred embodiments, the ankle plate 22 can be shaped, sized, configured and/or positioned in alternate manners with efficacy, as required or desired, Driving due consideration to the goal providing a suitably strong and generally natural feeling prosthetic foot 12, and/or of achieving one or more of the advantages and (benefits as taught or suggested herein.

The upper ankle plate 22 is preferably capable of flexing along its length. Desirably, the flexing of the ankle plate 22 under the weight of the amputee tends to distribute and/or relieve shear stresses applied at the interface between the ankle plate 22 and ankle block 24. Moreover, the flexing contributes to a more natural feeling walking and/or running stride for the wearer of the prosthetic foot 12.

In one preferred embodiment, the ankle plate 22 generally comprises an anterior section or portion 76, a medial section or portion 78 and a posterior section or portion 80. The front section 76 generally extends towards the toe region 46 of the lower foot plate 20 and the rear section 80 generally extends towards the heel region 50 of the lower foot plate 20.

Preferably, the ankle plate 22 is generally sized, shaped and/or configured to approximately simulate the dynamics of the upper portion of a natural human foot. Optionally, the ankle plate 22 can comprise a generally flat plate, as needed or desired.

Preferably, the ankle plate front section 76 is generally inclined or noses in a downward direction relative to a plane $P_3$ (FIG. 8) which is substantially perpendicular to a plane through the attachment axis 34. This nosing of the front section 76 generally simulates the structure of the upper portion of a natural human foot. Moreover, the downwards inclination of the front section 76 preferably generally follows the underlying contour of the upper surface of the foot plate 20. Advantageously, this results in a generally uniform thickness of the ankle block 24 material underneath the ankle plate front section 76. It has been determined that such a shape and/or configuration causes improved performance characteristics and longer durability with reduced chances of delamination, peeling or separation between the ankle block 24 and the plates 20, 22. Moreover, the downwards inclination of the front section 76 permits clearance space between the ankle plate front section 76 and the surrounding cosmesis 14 which can allow longer layers of the ankle block 24 to extend towards the foot plate toe region 46, as needed or desired. In other preferred embodiments, the ankle plate front section 76 can be shaped, sized and/or configured in alternate manners with efficacy, as required or desired, giving due consideration to the goals of providing improved performance characteristics, and/or of achieving one or more of the advantages and benefits as taught or suggested herein.

Preferably, the ankle plate front section 76 has a tapered thickness with the smallest thickness substantially at or near a front end 82 to allow more flexing of the ankle plate front section 76 near the front region of the ankle block 24. In other preferred embodiments, the ankle plate front section 76 can be shaped, sized and/or configured in alternate manners with efficacy, as required or desired, giving due consideration to the goals of providing improved performance characteristics, and/or of achieving one or more of the advantages and benefits as taught or suggested herein.

Preferably, the ankle plate front section 76 has a tapered width with the smallest width substantially at or near a front end 82. This substantially conforms to the configuration of the underlying ankle block 24 and also more closely simulates the structure of the upper portion of a natural human foot. In other preferred embodiments, the ankle plate front section 76 can be shaped, sized and/or configured in alternate manners with efficacy, as required or desired, giving due consideration to the goals of providing improved performance characteristics, and/or of achieving one or more of the advantages and benefits as taught or suggested herein.

In one preferred embodiment, the lower surface of the ankle plate front section 76 comprises a location rib or bump 86 for establishing the relative positioning between the ankle plate 22 and the ankle block 24. The location bump 86 mates with or engages a corresponding groove on the upper surface of the ankle block 24. The rib 86 may also provide added protection against separation, peeling or delamination between the ankle plate 22 and the ankle block 24.

Alternatively, the location rib may be provided on the ankle block 24 and the corresponding groove may be provided on the ankle plate 22. Additionally, other positioning means such as location pins and the like may be efficaciously used, as required or desired, giving due consideration to the goals of establishing the desired positioning between the ankle plate 22 and the ankle block 24, and/or of achieving one or more of the advantages and benefits as taught or suggested herein.

Preferably, the location rib 86 extends crosswise across the span of the lower surface of the ankle plate 22. In other preferred embodiments, the rib 86 (and corresponding groove) can be positioned and configured in alternate manners with efficacy, as required or desired, giving due consideration to the goals of establishing the desired positioning between the ankle plate 22 and the ankle block 24, and/or of achieving one or more of the advantages and benefits as taught or suggested herein.

The ankle plate medial section 78 is generally rectangular in shape and has top and bottom surfaces which are generally parallel to the plane $P_3$ (FIG. 8). Preferably, the middle section 78 is generally positioned above the flat upper surface 64 of the foot plate arch section 48. The width of the medial section 78 is generally about the same as the width of the foot plate 20 below it. In other preferred embodiments, the ankle plate fin medial section 78 can be shaped, sized, configured and/or positioned in alternate manners with efficacy, as required or desired, giving due consideration to the goals of providing improved performance characteristics, and/or of achieving one or more of the advantages and benefits as taught or suggested herein.

The ankle plate middle section 78 includes a through cavity or hole 88 extending between the lower and upper surfaces of the middle section 78 to receive a bolt or screw 30 and a washer 32 (FIG. 1). The fastening bolt 30 is used to secure the attachment member 28 (FIG. 1) to the ankle plate 22. The cavity 88 includes a lower cavity or hole 90 and an upper cavity or hole 92. The lower cavity 90 has a larger diameter compared to the diameter of the upper cavity 92 to receive a head 94 (FIG. 1) of the bolt 30 and the washer 32. The upper cavity 92 receives a shank or threaded portion 96 (FIG. 1) of the bolt 30.

The attachment member 28 connects the prosthetic foot 12 to a stump or lower leg pylon (not shown) of a wearer. The attachment member 28 is adapted to be fastened to the upper surface of the ankle plate middle section 78. Preferably, the upper surface of the ankle plate middle section 78 has a pair of central lengthwise grooves 98 (labeled 98a, 98b in FIGS. 6–8) which engage or mate with corresponding protrusions on the lower surface of the attachment member 28. Advantageously, this prevents or mitigates undesirable relative rotation and/or displacement between the ankle plate 22 and the attachment member 28.

Preferably, the grooves 98 are substantially V-shaped, though other shapes can be employed with equivalent efficacy. Alternatively, one or more grooves may be provided on the lower surface of the attachment member 28 and the corresponding mating protrusions on the upper surface of the ankle plate middle section 78, as required or desired, giving due consideration to the goals of preventing or mitigating relative rotation and/or displacement between the ankle plate 22 and the attachment member 28, and/or of achieving one or more of the advantages and benefits as taught or suggested herein.

In one preferred embodiment, the attachment member 28 comprises a male pyramid connector and includes a coupling knob 100 (FIG. 1) for mating with a coupling member on the pylon of the wearer. In the illustrated embodiment, the attachment member or pyramid connector 28 comprises a base plate 102 (FIG. 1), having the upstanding coupling knob 100 formed integrally therewith. The attachment member further may include a pair of upstanding location pins which help transmit torsional forces between the pylon and the foot prosthesis 12 and/or the prosthetic foot assembly 10.

A central threaded bore 104 (FIG. 1) in the knob 100 threadably receives the threaded portion or shank 96 of the fastening bolt 30 extending upwardly through the aperture 88 in the ankle plate middle section 78. Of course, other attachment members can be attached via the upwardly directed fastening bolt 30, as will be readily apparent to those of skill in the art. Moreover, other fastening means such as pins, locks, clamps and the like may be efficaciously used, as needed or desired. Advantageously, the head 94 of the upwardly directed fastening bolt 30 resides within the ankle plate 22 and the bolt 30 does not traverse the ankle block 24 or the foot plate 20. Thus, bolt receiving cavities or holes are not needed in the ankle block 24 and the foot plate 20. This can be particularly important in the case of the ankle block 24 since such cavities or holes formed within the ankle block 24 may adversely affect the compressible or resilient properties of the ankle block 24, and hence affect the performance characteristics of the prosthetic foot 12. Optionally, a downwardly directed bolt may be utilized so that the bolt head 94 is seated within the attachment member 28 and the threaded portion or shank 96 is threadably engaged with the ankle plate 22.

The ankle plate rear section 80 is generally rectangular in shape with generally curved side surfaces, and top and bottom surfaces which are generally parallel to the plane $P_3$ (FIG. 8). Preferably, the rear section 80 is generally positioned above the flat upper surface 64 of the foot plate arch section 48 and may also be positioned above part of the foot plate heel region 50. The major width of the rear section 80 is generally less than the width of the portions of the ankle block 24 and foot plate 20 below it. The major width of the rear section 80 is also generally less the width of the ankle plate medial section 78. In other preferred embodiments, the ankle plate posterior section 80 can be shaped, sized, configured and/or positioned in alternate manners with efficacy, as required or desired, giving due consideration to the goals of providing improved performance characteristics, and/or of achieving one or more of the advantages and benefits as taught or suggested herein.

Preferably, the limit strap or extension delimiter 26 (FIGS. 1–3) generally circumscribes portions of the ankle plate 22, ankle block 24 and foot plate 20 at or near the rear or heel of the prosthetic foot 12. The limit strap 26 is in contact with the upper surface of the ankle plate posterior section 80 and the lower surfaces of one or both of the foot plate arch section 48 and foot plate heel section 50. The strap 26 preferably forms a generally snug fit around the sandwiched assembly of the foot plate 20, ankle plate 22 and ankle block 24 though there are gaps or clearance spaces 106 between the strap 26 and the curved sides of the ankle plate rear section 80, as seen in FIG. 3.

The limit strap 26 serves to contain or control the separation to prevent delamination between the ankle block 24 and the plates 20, 22 at or near the heel of the prosthetic foot 12 during the heel-off portion of the amputee's stride, when the rear of the foot 12 undergoes maximum or high tension or stretching. The limit strap 26 desirably has an overlap 108 (FIG. 2) which is sewn using a cross-stitch of heavy thread. Although the strap 26 is shown with the overlapped portion 108 above the top surface of the ankle plate 22, it is understood that the overlap 108 may be positioned otherwise.

Preferably, the ankle plate 22 is fabricated from a vinyl ester based sheet molding compound, such as Quantum QC-8800, available from Quantum Composites of Midland, Michigan. The ankle plate 22 preferably comprises a vinyl ester resin matrix with a substantially randomly arranged fiberglass fiber content. In another preferred embodiment, the ankle plate 22 is constructed of fiberglass. Alternatively, the ankle plate 22 may be formed by a plurality of lamina embedded in a hardened flexible polymer. The ankle plate 22 can also be formed of carbon fibers.

In other arrangements, the ankle plate 22 may be formed of alternate suitable materials, such as other composite materials, plastics, thermoplastic and thermosetting polymers, metals, alloys and ceramics among others, as required or desired, giving due consideration to the goals of achieving one or more of the advantages and benefits as taught or suggested herein. The desirable properties of the ankle plate 22 are that it is relatively resilient so as to withstand cracking upon application of repeated bending m stresses, yet has sufficient flexibility to enhance the performance characteristics felt by the wearer, in conjunction with the properties of the resilient ankle block 24 and the foot plate 20.

Preferably, the ankle plate 22 is formed by a molding process. More preferably, the ankle plate 22 is formed by a compression molding process. Alternatively, the ankle plate 22 can be formed by an injection molding process. In other preferred embodiments, the ankle plate 22 can be fabricated using other techniques, for example, machining, welding, laminating, casting and forging among others, with efficacy, as required or desired, giving due consideration to the goals of providing enhanced performance, and/or of achieving one or more of the advantages and benefits as taught or suggested herein.

TABLE 3 below, in accordance with one preferred embodiment, lists various approximate dimensions of the ankle plate 22 for various amputee foot sizes. The number in the "SIZE" column in TABLE 3 refers to the cosmesis size or overall length in centimeters. The other column heading symbols in TABLE 3 refer to dimensional labels as marked on FIGS. 7–8. A, B, D, F, K refer to lengths (in inches), H, I refer to widths (in inches), and C, E refer to thicknesses. It will be appreciated that other dimensions than those of TABLE 3 may be used, as needed or desired.

TABLE 3

ANKLE PLATE DIMENSIONS FOR DIFFERENT FOOT SIZES (CORRESPONDS TO FIGS. 7 AND 8)

| SIZE | A | B | C | D | E | F | H | I | K |
|------|------|------|------|-----|-------|-------|------|------|------|
| 21–22 | 2.55 | 1.53 | .300 | .61 | .950 | 4.080 | 1.50 | 1.10 | 2.55 |
| 23–24 | 2.60 | 1.70 | .300 | .63 | .960 | 4.300 | 1.64 | 1.20 | 2.60 |
| 25–26 | 2.68 | 1.80 | .340 | .67 | .997 | 4.480 | 1.76 | 1.30 | 2.68 |
| 27–28 | 2.75 | 1.97 | .340 | .72 | 1.027 | 4.720 | 1.90 | 1.40 | 2.75 |

In one preferred embodiment, and referring to FIGS. 7 and 8, the length G1 is about 0.85 inches, the length G2 is about 1.70 inches, the thickness G3 is about 0.35 inches, the thickness G4 is about 0.12 inches, the length G5 is about 1.70 inches, the radius of curvature R1 is about 0.22 inches, the radius of curvature R2 is about 0.50 inches, the angle $\theta_{A1}$ is about 5°, the angle $\theta_{A2}$ is about 170°, the angle $\theta_{A3}$ is about 6°, the diameter of the cavity 92 is about 0.41 inches, the diameter of the cavity 90 is about 1.00 inches, the location rib 86 has a radius of curvature of about 0.19 inches and a height of about 0.06 inches, the grooves 98 have a depth of about 0.06 inches and a width of about 0.06 inches, the curved side surfaces of the rear section 80 have a radius of curvature of about 0.25 inches. The ankle plate 22 may be otherwise dimensioned, as needed or desired.

The bolt 30 is preferably a metric hex head bolt and preferably comprises stainless steel. The bolt 30 is cold formed with rolled threads and passivated. The minor diameter of the bolt head 94 is about 16.85 mm. The head 94 is about 6.30 mm thick. The shank 96 of the bolt 30 is about 30 mm long and comprises threads (M10–1.5) along its whole length. Alternatively, a wide variety of other bolts may be used with equivalent efficacy, as needed or desired.

The washer 32 is preferably flat and round and is formed from stainless steel. The washer 32 has a thickness of about 0.050 inches, an inner diameter of about 0.406 inches, and an outer diameter of about 0.875 inches. Alternatively, a wide variety of other washers may be used with equivalent efficacy, as needed or desired.

The attachment member or pyramid connector 28 is preferably formed from titanium or a titanium alloy such as TIMETAL 6S2, 6A1–4V titanium, or TI3-1. The pyramid connector has a major diameter of about 1.614 inches and a height of about 0.758 inches. The central threaded bore 104 of the connector 28 preferably comprises a M10-1.5 threaded through cavity. Alternatively, a wide variety of other attachment members may be used with equivalent efficacy, as needed or desired.

The limit strap 26 preferably comprises a thick natural tubular nylon webbing or a woven nylon having a thickness of about 0.078 inches and a width of about 0.75 inches. The overlap 108 is sewn with a box stitch overlap with "X", double back tack at both ends. A bonded polyester thread (Dabond) is used to create the overlap 108 with 8 stitches per inch. Alternatively, the overlap 108 can be stitched using a cross-stitch of heavy nylon thread. After cutting a strap of appropriate length from the raw material, the ends of the strap are melted.

For a foot size of 21–22, the strap 26 has an open (ends not overlapped) span of about 6.70 inches, an overlap 108 of about 1.10 inches, and an internal diameter of about 1.65 inches. For a foot size of 23–24, the strap 26 has an open (ends not overlapped) span of about 7.20 inches, an overlap 108 of about 1.20 inches, and an internal diameter of about 1.81 inches. For a foot size of 25–26, the strap 26 has an open (ends not overlapped) span of about 7.70 inches, an overlap 108 of about 1.30 inches, and an internal diameter of about 1.93 inches. For a foot size of 27–28, the strap 26 has an open (ends not overlapped) span of about 8.10 inches, an overlap 108 of about 1.40 inches, and an internal diameter of about 2.02 inches. The strap 26 can be dimensioned in alternate ways, as needed or required.

Compressible Ankle Block

Referring to the drawings, and in particular to FIGS. 1–3 and 10–12, the ankle block or cushion 24, is positioned intermediate the foot plate 20 and the ankle plate 22 and preferably comprises a monolithic element of material. Preferably, and as discussed in greater detail below, the lower surface of the ankle block 24 is bonded to the foot plate 20 and the upper surface of the ankle block 24 is bonded to the ankle plate 22 using an adhesive.

The ankle block or keel 24 is smaller in length than the foot plate 20 and longer than the ankle plate 22. The average and major widths of the ankle block 24 are smaller than the respective average and major widths of the foot plate 20. The average width of the ankle block 24 is slightly greater than the average width of the ankle plate 22 while the major width of the ankle block 24 is about the same as the major width of the ankle plate 22.

The ankle block 24 is preferably centered transversely with respect to the foot plate 20 and the ankle plate 22. Preferably, the ankle block 24 is generally positioned over the back portion of the arch section 48 of the lower foot plate 20 and under the length of the upper ankle plate 24. The ankle block 24 preferably extends substantially more forward of the attachment axis 34 (FIG. 1) than rearwardly. The contour of the lower surface of the ankle block 24 generally follows the contour of the portion of the upper surface of the foot plate 20 on which it is seated. The contour of the upper surface of the ankle block 24 generally follows the contour of the lower surface of the ankle plate 22.

In other preferred embodiments, the ankle block 24 can be shaped, sized, configured and/or positioned in alternate manners with efficacy, as required or desired, giving due consideration to the goals of providing a smooth and lifelike response during walking and/or running activities, and/or of achieving one or more of the advantages and benefits as taught or suggested herein.

Advantageously, the ankle block 24 provides a cushioning effect and expands (stretches in tension), contracts (compresses) and/or distorts under the weight of the amputee during heel-strike, flat footed, heel-off and toe-off stages of walking and running activities. During walking and/or strides, the majority of the compressive forces imparted by the wearer is absorbed by the ankle block 24, with a small portion being absorbed by the flexible lower foot plate 20 and flexible upper ankle plate 22 of the prosthetic foot 12.

In one preferred embodiment, the ankle block 24 generally comprises an anterior section or portion 116 and a posterior section or portion 120. The front section 116 generally extends towards the toe region 46 of the lower foot plate 20 and the rear section 120 generally extends towards the heel region 50 of the lower foot plate 20.

Preferably, an upper surface 122 of the ankle block front section 116 is inclined in a downward direction relative to a plane $P_4$ (FIG. 12) which is substantially perpendicular to a plane through the attachment axis 34. This downwards inclination of the upper surface 122 of the ankle block front section 116 generally corresponds to the downwards inclination of the lower surface of the ankle plate front section 76 (FIG. 8) and has advantages and benefits as discussed above. In other preferred embodiments, the ankle block front section 116 can be shaped, sized and/or configured in alternate manners with efficacy, as required or desired, giving due consideration to the goals of providing a smooth and lifelike response during walking and/or running activities, and/or of achieving one or more of the advantages and benefits as taught or suggested herein.

Preferably, a lower surface 124 of the ankle block front section 116 is curved to generally follow the curvature of the portion of the foot plate arch section 48 below it. Desirably, this results in a generally uniform thickness of the ankle block front section 116. Functional testing has shown that such a shape and/or configuration causes improved performance characteristics and longer durability with reduced chances of delamination, peeling or separation between the ankle block 24 and the plates 20, 22.

A downwardly sloping front end 126 of the ankle block 24 forms a face 128 connecting the upper and lower surfaces 122, 124 of the ankle block 24. The face 128 is inclined relative to the vertical or to the attachment axis 34 and extends downwardly from the ankle plate 22 to the foot plate 20. This particular shape of the ankle block 24 desirably contributes to a more uniform distribution and transfer of compression stress. The shorter length of the ankle plate 22 and the sloping front face 128 of the ankle block 24 tend to reduce shear stresses occurring near the front end or tip 82 of the ankle plate 22 which could otherwise cause undesirable delamination of the prosthetic foot 12.

Preferably, the ankle block front section 116 has a tapered width with the smallest width substantially at or near a front end 126. This tapered width generally conforms to the width of the overlying portion of the ankle plate 22. In other preferred embodiments, the ankle block front section 116 can be shaped, sized and/or configured in alternate manners with efficacy, as required or desired, giving due consideration to the goals of providing a smooth and life-like response during walking and/or running activities, and/or of achieving one or more of the advantages and benefits as taught or suggested herein.

Preferably, the upper surface 122 of the ankle block front section 116 comprises a crosswise location or positioning groove or notch 130 which mates with the location rib 86 of the ankle plate 22. As discussed above, the location groove 130 and the location rib 86 establish the desired relative positioning between the ankle plate 22 and the ankle block 24.

The ankle block rear section 120 has a top surface 132 and a bottom surface 134 which are generally parallel to the plane $P_4$ (FIG. 12). Preferably, the upper surface 132 is longer than the lower surface 134. The rear section 120 is generally positioned above the flat upper surface 64 of the foot plate arch section 48 and may also be positioned above part of the foot plate heel region 50. The width of the rear section 120 is generally about the same as the width of the foot plate 20 below it. In other preferred embodiments, the ankle block rear section 120 can be shaped, sized, configured and/or positioned in alternate manners with efficacy, as required or desired, giving due consideration to the goals of providing a smooth and life-like response during walking and/or running activities, and/or of achieving one or more of the advantages and benefits as taught or suggested herein.

Preferably, the lower surface 134 of the ankle block rear section 120 comprises a crosswise location or positioning groove or notch 140 which mates with the location rib 66 of the foot plate 20. As discussed above, the location groove 140 and the location rib 66 establish the desired relative positioning between the foot plate 20 and the ankle block 24.

A rear end 142 of the ankle block rear section 120 has a face 144 substantially parallel to the vertical or to the attachment axis 34. Preferably, a downwardly and inwardly sloping rear/lower face 146 of the rear end 142 connects the end face 144 to the lower face 134. This tapered or inclined face 146 results in a substantially wedged configuration below and above the inclined face 146. Advantageously, and as discussed below, such a configuration provides a high degree of "plantar flexion."

Preferably, the ankle block 24 is bonded to the foot plate 20 and ankle plate 22 using Loctite 4471 Instant Adhesive (Item# 44704) manufactured by Loctite, Inc. and as available from R. S. Hughs Co. of Anaheim, Calif. The Loctite adhesive is a medium viscosity, fast curing, single component Cyanoacrylate adhesive which is formulated for difficult to bond substrates. Preferably, before the use of the adhesive, the surfaces to be adhered are cleansed of any oils, degreased, abraded and cleaned. Alternatively, other suitable adhesives, glues, or adhering materials and techniques can be used with equivalent efficacy.

A preferred material for the ankle block 24 is polyurethane foam such as Purcell Cellular Vulkollan Polyurethane, as available from Pleiger Plastics Company of Washington, Penn. Preferably, the polyurethane foam is a NDI/Polyester based polyurethane foam and has a high load capacity, is abrasion and tear resistant, and has a high elasticity with low permanent deformation. Alternatively, the ankle block 24 may comprise other suitable resilient materials such as natural or synthetic rubber, plastics, honeycomb structures or other materials.

Cellular foam, however, provides a desirable viscoelastic springiness for a more natural feeling stride without the drawback of limited compression associated with solid elastomeric materials. Furthermore, the cellular nature of the ankle block 24 makes it lighter than solid elastomers. Foam densities between about 150 and 1500 kg/m$^3$ may be used to obtain the benefits of the invention taught herein.

The ankle block 24 provides a relatively stiff, yet flexible ankle region which may be customized for various wearers. Heavier wearers may require a denser and/or thicker resilient material for the ankle block 24, while lighter wearers may require a less dense material or less thickness. More detailed material specifications and dimensions are presented later herein.

Preferably, the ankle block 24 is machined out of larger blocks or units of material which are formed by molding. The machining preferably comprises a water jet processing and can be performed by Pleiger Plastics Company of Washington, Penn. Preferably, any "molded skin" which is formed at the tool-block interface during the molding of the larger blocks or units and remains on the ankle block 24 is skived or sheared off the ankle block 24 while ensuring the correct dimensions.

The "molded skin" can cause non-uniformity in the resilient and/or compressible characteristics of the ankle block 24. Moreover, it may make the adhesion of the ankle block 24 to the plates 20, 22 more difficult. In one preferred embodiment, molded skin is not allowed on any of the surfaces of the ankle block 24. In another preferred embodiment, molded skin is allowed on the side surfaces of the ankle block 24 but not on the top and bottom surfaces.

In an alternative preferred embodiment, the ankle block 24 is formed by an injection molding process to achieve the desired shape, size and/or configuration. In other preferred embodiments, other techniques can be efficaciously utilized, as required or desired, giving due consideration to the goals of providing a smooth and life-like response during walking and/or running activities, and/or of achieving one or more of the advantages and benefits as taught or suggested herein.

Preferably, the surfaces of the ankle block 24 exposed to the atmosphere, that is, the side surfaces are treated or coated with a sealant to prevent moisture absorption over time due to the micro-cellular nature of the preferred material forming the ankle block 24. The absorption of moisture over time can change and/or cause unpredictability in the dynamic characteristics of the ankle block 24.

Preferably, E-6000 MV Clear (Non-flammable) Sealant (Product Code 371000130) manufactured by Eclectic Products, Inc. and as available from Ellsworth Adhesive Systems of Tustin, Calif. is applied to the exposed surfaces of the ankle block 24. This sealant is preferably used in conjunction with a sealant thinner or solvent containing tetrachlorodethylene (perchloroethylene) manufactured by PPG Industries, Inc. and as available from Gallade Chemical, Inc. of Santa Ana, Calif. In other preferred embodiments, alternate sealants and/or thinners may be efficaciously used, as required or desired, giving due consideration to the goals of preventing or mitigating moisture absorption by the ankle block 24, and/or of achieving one or more of the advantages and benefits as taught or suggested herein.

TABLE 4 below, in accordance with one preferred embodiment, lists various approximate dimensions of the ankle block 24 for various amputee foot and weight sizes. The number and letter in the "SIZE" column in TABLE 4 respectively refer to the cosmesis size or overall length in centimeters and the weight group (L=Light, M=Medium, H=Heavy) of the amputee. The "Manuf. ID" refers to the part identification for blocks of Purcell Cellular Vulkollan Polyurethane as available from Pleiger Plastics Company of Washington, Penn. and from which the ankle block 24 is fabricated to the required design. The other column heading symbols in TABLE 4 refer to dimensional labels as marked on FIGS. 11–12 and to the weight of the ankle block 24. B, C, D, E, H, J refer to length scales (in inches), A refers to a width (in inches), L refers to a thickness (in inches), and M refers to a radius of curvature (in inches). Note that the H dimension is tangent to the radius of curvature of the surface 124 and/or extends upto the beginning of the curvature of the surface 124. It will be appreciated that other dimensions and material specifications than those of TABLE 4 may be used, as needed or desired.

block 24 transmits the forces imparted thereon by the foot plate 20 and the ankle plate 22 such that the rollover or migration of the compressed region of the ankle block 24 is gradual and natural as felt by the amputee, as energy is cyclically stored and released the prosthetic foot 12.

During heel-strike, the weight of the amputee is initially transmitted to the heel of the leading foot, and the compressive stresses are absorbed by the rear region 120 of the ankle

TABLE 4

ANKLE BLOCK DIMENSIONS AND WEIGHTS FOR DIFFERENT AMPUTEE SIZES (CORRESPONDS TO FIGS. 11 AND 12)

| SIZE | Manuf. ID | A | B | C | D | E | H | J | L | M | Ankle Block Weight (Grams) |
|---|---|---|---|---|---|---|---|---|---|---|---|
| 21–22L | 15–40 | 1.50 | 4.32 | 2.55 | 1.55 | .60 | 2.58 | 2.33 | .92 | 5.75 | 25–30 |
| 21–22H | 15–45 | 1.50 | 4.32 | 2.55 | 1.55 | .60 | 2.58 | 2.33 | .92 | 5.75 | 31–36 |
| 23–24L | 15–40 | 1.64 | 4.57 | 2.60 | 1.73 | .64 | 2.59 | 2.34 | 1.00 | 7.00 | 32–37 |
| 23–24M | 15–45 | 1.64 | 4.57 | 2.60 | 1.73 | .64 | 2.59 | 2.34 | 1.00 | 7.00 | 38–42 |
| 23–24H | 15–50 | 1.64 | 4.57 | 2.60 | 1.73 | .64 | 2.59 | 2.34 | 1.00 | 7.00 | 43–49 |
| 25–26L | 15–45 | 1.76 | 4.73 | 2.68 | 1.83 | .70 | 2.75 | 2.50 | 1.00 | 8.75 | 41–46 |
| 25–26M | 15–50 | 1.76 | 4.73 | 2.68 | 1.83 | .70 | 2.75 | 2.50 | 1.00 | 8.75 | 47–52 |
| 25–26H | 15–55 | 1.76 | 4.73 | 2 68 | 1.83 | .70 | 2.75 | 2.50 | 1.00 | 8.75 | 53–59 |
| 27–28L | 15–45 | 1.90 | 4.97 | 2.75 | 2.00 | .75 | 2.75 | 2.50 | 1.00 | 9.50 | 48–53 |
| 27–28H | 15–50 | 1.90 | 4.97 | 2.75 | 2.00 | .75 | 2.75 | 2.50 | 1.00 | 9.50 | 54–60 |

In one preferred embodiment, and referring to FIGS. 11 and 12, the thickness Q1 is about 0.25 inches, the angle $\theta_{B1}$ is about 5°, the angle $\theta_{B2}$ is about 10°, the angle $\theta_{B3}$ is about 15°, the angle $\theta_{B4}$ is about 60°, the location grooves 130, 140 have a radius of curvature of about 0.19 inches and a depth of about 0.06 inches. The ankle plate 22 may be otherwise dimensioned, as needed or desired. For instance, other angles $\theta_{B3}$ ranging from about 5° to about 45° and other angles $\theta_{B4}$ ranging from about 45° to about 75° may be used to achieve the benefits taught herein.

As indicated above, in one preferred embodiment, the ankle blocks 24 are formed from larger blocks or block units of Purcell Cellular Vulkollan Polyurethane as available from Pleiger Plastics Company of Washington, Penn. One preferred block size has dimensions of 55 (+3/−2) mm×250 (±5) mm×500 (+10/−3) mm and is referred to as Block A in the TABLE 5 below. Another optional block size has dimensions of 55 (+3/−2) mm×250 (±5) mm×750 (+10/−3) mm and is referred to as Block B in the TABLE 5 below. TABLE 5 lists material and property specifications for Purcell Cellular Vulkollan Polyurethane as available from Pleiger Plastics Company of Washington, Penn.

block 24 at or near the rear end 142. As the amputee continues through his/her stride, the compression of the ankle block 24 travels smoothly and continuously toward the front portion 116 or end 126 of the ankle block 24 during the flat-foot position and leading to the heel-off position. In the toe-off position the ankle block 24 starts to resume its original (uncompressed) state as some of the weight of the amputee is being transferred to the opposite foot, which has now moved forward. The ankle block 24 resumes its original shape as the amputee lifts his/her leading foot of the ground or supporting surface. Advantageously, the dynamics of such a stride give the foot a natural feel.

During heel-strike, the heel section 50 of the foot plate 20 bends to some degree and a slight amount of bending may occur at the rear section 80 of the ankle plate 22. In the heel-off position, the toe section 46 of the foot plate 20 bends to some degree and the front section 76 of the ankle plate 22 may bend slightly. In the toe-off position there is less bending if any of both the foot plate toe section 46 and the ankle plate front section 76.

It is important to note that although the ankle block 24 absorbs a majority of the compression generated by the

TABLE 5

MATERIAL SPECIFICATION FOR PURCELL CELLULAR VULKOLLAN POLYURETHANE

| Manuf. ID | Weight Block A (grams) | Weight Block B (grams) | Density (kg/m$^3$) | Tensile Strength (N/mm$^2$) | Elongation (%) | Tear (kN/m) | Rebound (%) | Hardness Shore A |
|---|---|---|---|---|---|---|---|---|
| 15–35 | 2179–2358 | 3269–3537 | 317–343 | 4.00 | 390 | 8 | 70 | 20–30 |
| 15–40 | 2509–2716 | 3764–4073 | 365–395 | 4.50 | 410 | 10 | 70 | 25–35 |
| 15–45 | 2839–3073 | 4259–4610 | 413–447 | 5.50 | 430 | 12 | 70 | 30–40 |
| 15–50 | 3169–3431 | 4754–5146 | 461–499 | 6.50 | 450 | 14 | 70 | 35–45 |
| 15–55 | 3499–3788 | 5249–5682 | 509–551 | 7.50 | 465 | 18 | 70 | 40–50 |
| 15–60 | 3829–4146 | 5744–6218 | 557–603 | 8.00 | 470 | 20 | 70 | 45–55 |

Prosthetic Foot Dynamics

The prosthetic foot 12 of the invention provides a particularly smooth and life-like response during normal walking or running activities. The uniquely configured ankle wearer, the flexible foot plate 20 and the flexible ankle plate 22 are designed to work in conjunction with the resilient ankle block 24 and provide enhanced dynamic performance.

Another advantage is provided by the high degree of "plantar flexion" due to the wedged configuration of the rear end 142 of the ankle block 24. Referring in particular to FIGS. 1, 5 and 12, this wedged configuration or inward taper of the face 146 results in an increased and/or predetermined distance between the foot plate heel end 62 (and heel region 50) and a contact axis 150 formed at the contact location between the taper 146 of the ankle block 24 and the upper surface of the lower foot plate 20. Advantageously, during heel-strike, this effectively results in a longer moment, lever or cantilever arm between the heel end 62 (and heel region 50) and the effective fulcrum point or axis (which is at or close to the contact axis 150). Desirably, this translates into more downward deflection of the toe end 60 (and toe region 46) caused by more upward deflection of the heel end 62 (and heel region 50) or "plantar flexion."

At heel-strike, the flexible heel member 50 bends to absorb the amputee's walking or running energy. This energy is substantially uniformly transmitted to the flexible forefoot member 46, causing it to deflect downward before the toe makes contact with the ground surface. Also, the subjection of the heel member or region 50 to bending moments causes transmission of spring stress through the heel region 50 to the forefoot or toe region 46 whereby an energy return effect is achieved. This results in smoother rollover and a better overall feel as the amputee's weight more smoothly shifts forward from heel (heel-strike) to toe (heel-off). Absent such deflection of the forefoot region 46, there is a greater delay between heel-strike and toe strike (heel-off), resulting in relatively unsmooth rollover.

Thus, the high degree of plantar flexion achieved by the prosthetic foot 12 of the present invention adds to providing a more smooth and life-like response during normal walking or running activities. The wedged or taper feature of the ankle block 24 can be adjusted or selectively dimensioned and configured, as required or desired, giving due consideration to the goals of providing a more natural walking and/or running feel and improved rebounding and responsiveness, and/or of achieving one or more of the advantages or benefits as taught or suggested herein.

Although not illustrated, the prosthetic foot 12 of the present invention can also provide enhanced performance for the wearer in inversion or eversion. The present invention allows the amputee to walk transversely upon sloped surfaces, for example, with the foot plate 20 generally conforming to the terrain while the ankle plate 22 remains relatively horizontal due to the sideways compression of the ankle block 24. Again, as the wearer lifts his or her foot 12, the ankle block 24 resumes its original shape, thus helping the wearer as energy is stored and then released.

It can now be appreciated that the "feel" of the present prosthetic foot 12 is greatly enhanced by the cooperation between foot plate 20, ankle plate 22, and ankle block 24. As the wearer continues through the walking stride, the dynamic response from the prosthetic foot 12 is smooth as the ankle block 24 compresses in different regions and a high degree of plantar flexion is achieved. Further, the flexing of the foot plate 20 and ankle plate 22 also assist in smoothly transmitting the various bumps and jars found in uneven walking surfaces.

Outer Cosmesis

Figure 13:
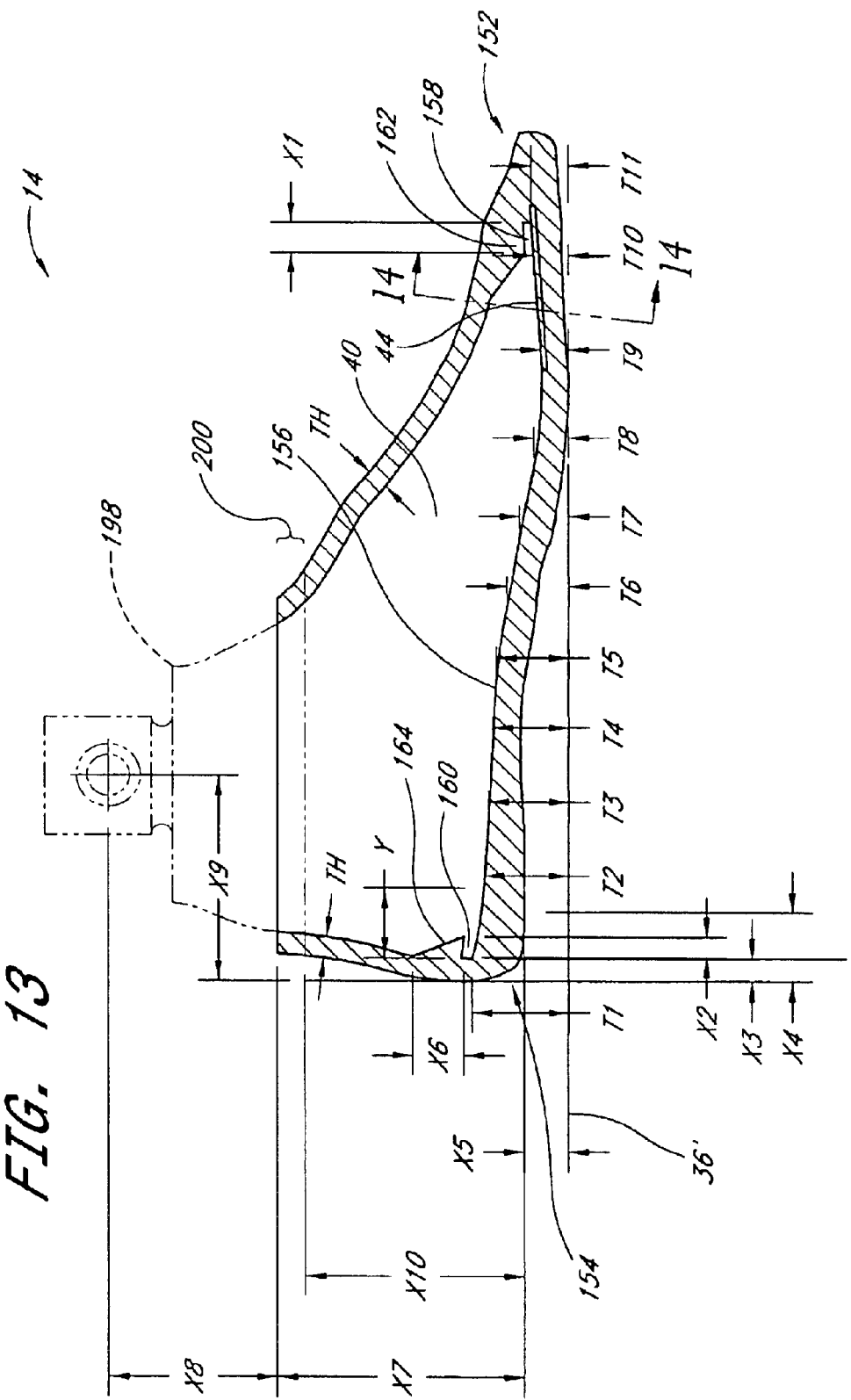
FIG. 13 is a sectional view of an outer cosmesis (along substantially a longitudinal axis of the cosmesis) of the prosthetic foot assembly of FIG. 1 having features in accordance with one preferred embodiment of the present invention.
Figure 17:
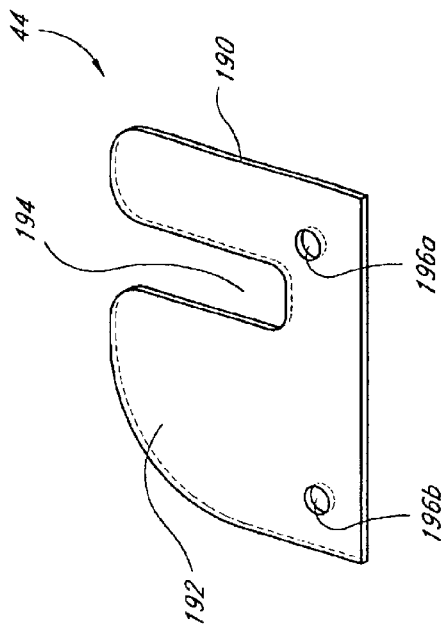
FIG. 17 is a perspective view of a reinforcement patch of the cosmesis of FIG. 13.
Figure 18:
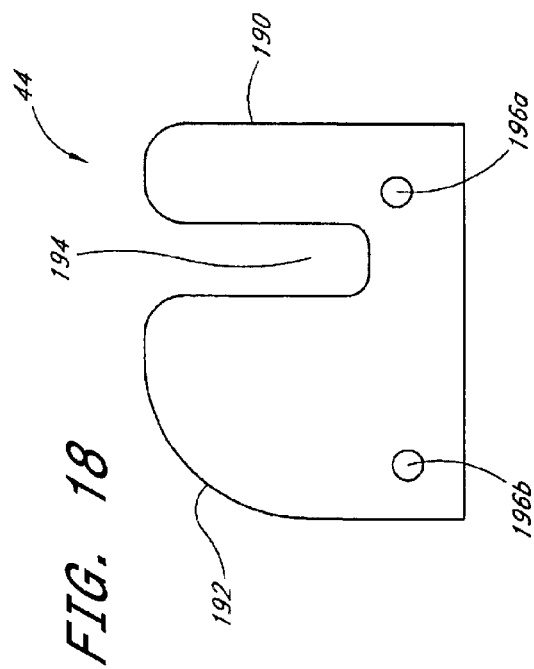
FIG. 18 is a top plan view of the reinforcement patch of FIG. 17.
Figure 19:
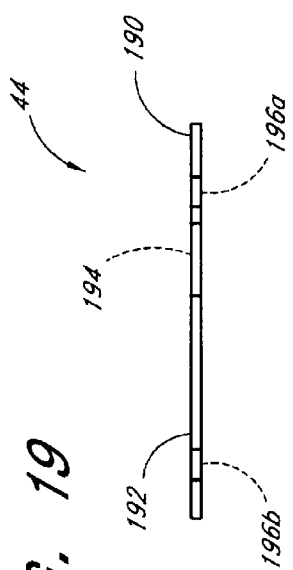
FIG. 19 is a rear view of the reinforcement patch of FIG. 17.

Referring to the drawings, and in particular to FIGS. 1–2 and 13–16, the flexible cosmesis 14 is an outer cover for a prosthetic foot, such as the prosthetic foot 12, and is an approximate replicate of the appearance of a human anatomical foot. FIG. 13 shows an imaginary plane 36' which is upwardly offset from the supporting ground surface 36 of FIG. 1 and is tangential to the lower surface of the cosmesis 14 near the toe region. The orientation of the cosmesis 14 with respect to the plane 36' is indicative of a sole and/or heel of a shoe or other footwear worn by the amputee over the cosmesis 14.

The cosmesis 14 is preferably fabricated from a flexible material and provides an auxiliary or complementary cushioning effect. The cosmesis 14 generally comprises an anterior or front toe region 152, a posterior or rear heel region 154 and the inner cavity 40 which includes an inner sole 156. The cavity 40 is adapted to receive a prosthetic foot, such as the prosthetic foot 12. The sole 156 is shaped, sized and configured to conform to the general shape, size and configuration of the lower foot plate 20.

Preferably, the cavity 40 further comprises a slotted region 158 at the toe portion 152 of the cosmesis 14 and a slotted region or slot 160 at the heel portion 154 of the cosmesis 14. The slotted region 158 is formed under an extending section 162 and is adapted to receive the foot plate toe section 46. The slotted region 160 is formed under an extending section or protrusion 164 and is adapted to receive the foot plate heel section 50.

The toe region 152 of the cosmesis 14 comprises a big toe 166, an adjacent small toe 168 and three other small toes 170, 172, 174. In one preferred embodiment, the slit or slot 42 between the big toe 166 and adjacent toe 168 is provided to receive a thong or 0 the like of a thong sandal or other footwear. Optionally, slits or slots may also be provided between the small toes 168, 170, 172, 174, as needed or desired.

The cosmesis inner sole 156 comprises a pair of toe seating portions 176, 178 at the toe region 152 of the cosmesis 14. The toe seating portions 176, 178 are separated by an intermediate raised portion 184 and the thong-receiving slot 42. The sole toe portion 176 is wider than the sole toe portion 178 and is configured to seat one of the outer toes of the foot plate 20 and the central toe of the foot plate 20, such as the outer toe 52a and the central toe 52c. The smaller sole toe portion 178 is configured to receive an outer toe of the foot plate 20, such as the outer toe 52b. The raised portion or member 184 is received in one of the slots 54 between the toes 52. Advantageously, because of the symmetric toe configuration of the foot plate 20, as the skilled artisan will recognize, the prosthetic foot 12 may be used with either a left or a right foot cosmesis 14. Desirably, this adds to the versatility of the invention.

The inner slotted region 158 comprises a pair of toe receiving slots 180, 182 at the toe region 152 of the cosmesis 14. The toe receiving slots 180, 182 are separated by an intermediate raised portion 184 and the thong-receiving slot 42. The slot 180 is wider than the slot 182 and is configured to receive one of the outer toes of the foot plate 20 and the central toe of the foot plate 20, such as the outer toe 52a and the central toe 52c. The smaller slot 182 is configured to receive an outer toe of the foot plate 20, such as the outer toe 52b. The raised portion or member 184 is received in one of the slots 54 between the toes 52. Advantageously, because of the symmetric toe configuration of the foot plate 20, as the skilled artisan will recognize, the prosthetic foot 12 may be used with either a left or a right foot cosmesis 14. Desirably, this adds to the versatility of the invention.

The thong-receiving slot 42 of the cosmesis 14 can be shaped, sized and/or configured in a wide variety of manners. In one preferred embodiment, the slot 42 is substantially V-shaped. In another preferred embodiment, the slot 42 is substantially U-shaped. Other suitable shapes may also be utilized with equivalent efficacy, as needed or desired.

The reinforcement patch or strap 44 is provided in the toe region 152 of the cosmesis 14. The reinforcement patch 44 provides a durable barrier between the foot plate 20 and the cosmesis 14 and prevents or reduces wear of the sole 156 of the cosmesis 14 due to frictional contact and/or compression stresses. The patch 44 may be directly exposed to the foot plate toe region 46 and/or the foot plate 20 and thus be part of the sole 156, or it may be covered by a thin layer of the material forming the cosmesis 14 and hence be slightly under the sole 156. Alternatively, some portion(s) of the patch 44 may be directly exposed to the foot plate toe region 46 and/or the foot plate 20 and thus be part of the sole 156 and some portion(s) may be covered by a thin layer of the material forming the cosmesis 14 and hence be slightly under the sole 156. Some or all of the edges of the patch 44 can be embedded in the material forming the cosmesis 14.

The reinforcement patch 44 preferably comprises a first supporting section or portion 190 and a wider second supporting section or portion 192 with a slit or slot 194 formed therebetween. The narrower first supporting section 190 is generally aligned with the sole toe portion 178 and lies below or is generally aligned with one outer foot plate toe 52. The wider second supporting section 192 is generally aligned with the sole toe portion 176 and lies below or is generally aligned with two adjacent foot plate toes 52.

The patch slot 194 is substantially aligned with the thong-receiving slot 42. The patch slot 194 is also aligned with one of the slots 54 formed between the foot plate toes 52. The patch slot 194 is further aligned with the raised portion 184 between the sole toe portions 176, 178.

The slot 194 of the reinforcement patch 44 can be shaped, sized and/or configured in a wide variety of manners. In one preferred embodiment, the slot 194 is substantially U-shaped. In another preferred embodiment, the slot 42 is substantially V-shaped. Other suitable shapes may also be utilized with equivalent efficacy, as needed or desired.

The reinforcement patch 44 also includes a pair of spaced registration holes 196 (labeled 196a, 196b) which assist in positioning the patch 44 in the desired position during fabrication of the cosmesis 14. More than two registration holes 196 may be used, as needed or desired. Also, other registration means such as registration pins may be used with equivalent efficacy.

Preferably, the foot plate 20 is bonded to the cosmesis inner sole 156 (which may include exposed portions of the reinforcement strap 44) using Loctite 4471 Instant Adhesive (Item# 44704) manufactured by Loctite, Inc. and as available from R. S. Hughs Co. of Anaheim, Calif. The Loctite adhesive is a medium viscosity, fast curing, single component Cyanoacrylate adhesive which is formulated for difficult to bond substrates. Preferably, before the use of the adhesive, the surfaces to be adhered are cleansed of any oils, degreased, abraded and cleaned. Alternatively, other suitable adhesives, glues, or adhering materials and techniques can be used with equivalent efficacy.

The cosmesis 14 is preferably fabricated from a urethane material such as urethane foam. Alternatively, the cosmesis 14 may comprise other suitable resilient materials such as natural or synthetic rubber, plastics, honeycomb structures or other materials.

The cosmesis 14 is preferably formed using a molding process such as injection molding or insert molding. The molding utilizes an anatomically sculpted foot shape or mold, with details and sizing based on a master pattern and/or digitized data representing typical foot sizes. The molded density is approximately 25 lb/ft$^3$, though in other embodiments it may be less or more, as needed or desired.

A core part or tooling mandrel 198 (shown in phantom in FIG. 13) is preferably utilized during the fabrication/molding of the cosmesis 14. After the molding process a predetermined length or quantity of material 200 (FIG. 13) may be removed or cut off by machining to finalize the sizing of the cosmesis.

The registration holes 196 of the reinforcement patch 44 are engaged by a suitable tool or molding cone to orient and/or position the patch 44 in the proper orientation and position during the molding process. Desirably, the molding process also causes the reinforcement patch 44 to be firmly bonded in place. As indicated above, the surface of the patch 44 may be exposed, fully covered or partially covered after the molding is completed.

The reinforcement strap 44 is preferably fabricated from a polyurethane impregnated belting (Supplier Part No. FN1–12E) as available from California Industrial Rubber Co. of Fresno, Calif. This material generally comprises a urethane or polyurethane core and a polyester casing, and has a tensile strength of 780 lb/in and undergoes 1% elongation under a tensile force of 68 lb/in. Alternatively, other suitably strong materials may be utilized, as needed or desired. Preferably, the strap 44 is formed by stamping and/or punching operations, though other techniques such as machining among others can be used, as needed or desired.

TABLE 6 below, in accordance with one preferred embodiment, lists various approximate dimensions of the cosmesis 14 (and other related dimensions that may be used during molding of the cosmesis 14) for various amputee foot sizes. The number in the "SIZE" column in TABLE 6 refers to the cosmesis size or overall length in centimeters and the letter refers to the foot (L=Left, R=Right). The other column heading symbols in TABLE 6 refer to dimensional labels as marked on FIGS. 13 AND 16. All dimensions in TABLE 6 are in inches. Note that the dimensions T1 to T11 are taken at positions spaced by the corresponding value of Y, that is, the position at which T1 is taken is spaced from the position where T2 is taken by Y, and so on. It will be appreciated that other dimensions than those of TABLE 6 may be used, as needed or desired.

TABLE 6

COSMESIS DIMENSIONS FOR DIFFERENT FOOT SIZES
(CORRESPONDS TO FIGS. 13 AND 16)

| SIZE | TH | A | Y | T1 | T2 | T3 | T4 | T5 | T6 | T7 | T8 | T9 | T10 | T11 |
|---|---|---|---|---|---|---|---|---|---|---|---|---|---|---|
| 21L | .20 | 1.33 | .79 | .98 | .85 | .78 | .73 | .71 | .63 | .43 | .29 | .30 | .33 | |
| 21R | .20 | 1.33 | .79 | .98 | .85 | .78 | .73 | .71 | .63 | .43 | .29 | .30 | .33 | |
| 22L | .20 | 1.41 | .79 | .98 | .85 | .78 | .73 | .71 | .63 | .43 | .29 | .30 | .33 | .38 |
| 22R | .20 | 1.41 | .79 | .98 | .85 | .78 | .73 | .71 | .63 | .43 | .29 | .30 | .33 | .38 |

TABLE 6-continued

COSMESIS DIMENSIONS FOR DIFFERENT FOOT SIZES
(CORRESPONDS TO FIGS. 13 AND 16)

| SIZE | TH | A | Y | T1 | T2 | T3 | T4 | T5 | T6 | T7 | T8 | T9 | T10 | T11 |
|------|-----|------|------|------|-----|-----|-----|-----|-----|-----|-----|-----|------|-----|
| 23L | .20 | 1.49 | .86  | 1.04 | .90 | .82 | .75 | .75 | .68 | .51 | .37 | .32 | .39  |     |
| 23R | .20 | 1.49 | .86  | 1.04 | .90 | .82 | .75 | .75 | .68 | .51 | .37 | .32 | .39  |     |
| 24L | .20 | 1.57 | .86  | 1.04 | .90 | .82 | .75 | .75 | .68 | .51 | .37 | .32 | .39  | .44 |
| 24R | .20 | 1.57 | .86  | 1.04 | .90 | .82 | .75 | .75 | .68 | .51 | .37 | .32 | .39  | .44 |
| 25L | .24 | 1.65 | .93  | .94  | .83 | .73 | .69 | .68 | .58 | .45 | .34 | .32 | .40  |     |
| 25R | .24 | 1.65 | .93  | .94  | .83 | .73 | .69 | .68 | .58 | .45 | .34 | .32 | .40  |     |
| 26L | .24 | 1.73 | .93  | .94  | .83 | .73 | .69 | .68 | .58 | .45 | .34 | .32 | .40  | .47 |
| 26R | .24 | 1.73 | .93  | .94  | .83 | .73 | .69 | .68 | .58 | .45 | .34 | .32 | .40  | .47 |
| 27L | .24 | 1.81 | 1.00 | .90  | .80 | .72 | .66 | .62 | .53 | .36 | .25 | .25 | .34  |     |
| 27R | .24 | 1.81 | 1.00 | .90  | .80 | .72 | .66 | .62 | .53 | .36 | .25 | .25 | .34  |     |
| 28L | .28 | 1.88 | 1.00 | .90  | .80 | .72 | .66 | .62 | .53 | .36 | .25 | .25 | .34  | .40 |
| 28R | .28 | 1.88 | 1.00 | .90  | .80 | .72 | .66 | .62 | .53 | .36 | .25 | .25 | .34  | .40 |

In one preferred embodiment, and referring to FIG. 13, X1 is about 0.40 inches, X2 is about 0.13 inches, X3 is about 0.40 inches, X4 is about 1.00 inches, X5 is about 0.375 inches, X6 is about 0.75 inches, X7 is about 3.10 inches, X8 is about 2.00 inches, X9 is about 4.93 inches, and X10 is about 2.40 inches. The cosmesis 14 and other length scales of FIG. 13 may be otherwise dimensioned, as needed or desired.

For foot sizes 21–24, the reinforcement patch 44 has a thickness of about 0.060 inches, a major length of about 1.96 inches and a major width of about 2.21 inches. The narrow section 190 has a width of about 0.49 inches and the wide section 192 has a width of about 1.27 inches. The slot 194 has a length of about 1.37 inches and a width of about 0.45 inches. The registration holes 196 have a diameter of about 0.19 inches and are spaced by about 1.76 inches. The spacing between the holes 196 and the rear edge of the patch 44 is about 0.26 inches. The spacing between the hole 196b and the proximate side edge of the patch 44 is about 0.19 inches. The spacing between the hole 196a and the proximate side edge of the patch 44 is about 0.26 inches. In other embodiments, the patch 44 can be alternately dimensioned, as needed or desired.

For foot sizes 25–28, the reinforcement patch 44 has a thickness of about 0.060 inches, a major length of about 1.96 inches and a major width of about 2.48 inches. The narrow section 190 has a width of about 0.63 inches and the wide section 192 has a width of about 1.40 inches. The slot 194 has a length of about 1.37 inches and a width of about 0.45 inches. The registration holes 196 have a diameter of about 0.19 inches and are spaced by about 1.71 inches. The spacing between the holes 196 and the rear edge of the patch 44 is about 0.35 inches. The spacing between the hole 196b and the proximate side edge of the patch 44 is about 0.34 inches. The spacing between the hole 196a and the proximate side edge of the patch 44 is about 0.43 inches. In other embodiments, the patch 44 can be alternately dimensioned, as needed or desired.

While the components and techniques of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A prosthetic foot for providing a smooth and generally life like response to a wearer, comprising:
   a foot plate comprising a plurality of symmetrically arranged spaced elongated toes;
   an ankle plate positioned above said foot plate; and
   a compressible block between said foot plate and said ankle plate and in mechanical communication with said foot plate and said ankle plate for transmitting forces imparted thereon by said foot plate and said ankle plate such that there is a smooth and natural rollover between heel-strike and toe-off as energy is cyclically stored and released in said prosthetic foot, said block having exposed sides coated with a sealant.

2. The prosthetic foot of claim 1, wherein said foot plate has a generally curvilinear shape.

3. The prosthetic foot of claim 1, wherein said foot plate is capable of flexing along its length.

4. The prosthetic foot of claim 1, wherein said foot plate comprises a vinyl ester based sheet molding compound.

5. The prosthetic foot of claim 1, where said toes of said foot plate are slightly upwardly curved.

6. The prosthetic foot of claim 1, wherein said foot plate comprises a middle toe and two outer toes.

7. The prosthetic foot of claim 6, wherein said outer toes are slightly inwardly curved.

8. The prosthetic foot of claim 1, wherein said ankle plate has an anterior section inclined in the direction towards said foot plate.

9. The prosthetic foot of claim 1, wherein said ankle plate is capable of flexing along its length.

10. The prosthetic foot of claim 1, wherein said ankle plate comprises a vinyl ester based sheet molding compound.

11. The prosthetic foot of claim 1, further comprising a connector coupled to said ankle plate for facilitating attachment of said prosthetic foot to a socket or pylon of the wearer.

12. The prosthetic foot of claim 1, further comprising a strap generally circumscribing said foot plate, said ankle plate and said block to control the stretching of said blocks.

13. The prosthetic foot of claim 1, wherein said block comprises a downwardly and outwardly sloping front face.

14. The prosthetic foot of claim 1, wherein said block comprises a downwardly and inwardly sloping rear surface.

15. The prosthetic foot of claim 1, wherein said block comprises a monolithic element.

16. The prosthetic foot of claim 1, wherein said block comprises polyurethane foam.

17. The prosthetic foot of claim 1, wherein said block comprises cellular foam.

18. The prosthetic foot of claim 1, wherein said block ha a density between about 150 kg/m³ to about 1500 kg/m³.

19. The prosthetic foot of claim 1, wherein said block has a density between about 300 kg/m³ to about 600 kg/m³.

20. The prosthetic foot of claim 1, further comprising an outer cosmesis housing said foot plate, said ankle plate and said block.

21. The prosthetic foot of claim 20, wherein said cosmesis comprises a toe region with a slot to form a big toe substantially aligned with one of said toes of said foot plate.

22. The prosthetic foot of claim 21, wherein said toe region of said cosmesis comprises a reinforcement strap.

23. The prosthetic foot of claim 22, wherein said reinforcement strap has a slot substantially aligned with said slot of said toe region of said cosmesis.

24. An artificial foot for providing a smooth and natural dynamic response during walking or running activities of a lower limb amputee, comprising:
  a flexible lower foot plate having an upper surface and a lower surface, said foot plate comprising a toe section, an arch section and a heel section, said toe section comprising a plurality of toes spaced by a plurality of slots and a generally concave upward toe end, said arch section comprising a generally concave downward arch, said heel section comprising a generally concave upward heel end;
  a flexible upper ankle plate having a top surface and a bottom surface and a length shorter than said foot plate, said bottom surface of said ankle plate being substantially parallel to said upper surface of said foot plate, said ankle plate being connected to an attachment member utilizing a bolt for facilitating attachment to a stump or pylon of the amputee, said bolt hog a longitudinal axis defining an attachment axis generally aligned with the vertical centerline of an imaginary ankle; and
  a resilient ankle member composed of a compressible material and sandwiched between said foot plate and said ankle plate, said ankle member comprising an anterior section and a posterior section, said anterior section having a downwardly and outwardly sloping front face, said posterior section having a wedge shaped cut to form a first rear face substantially parallel with said attachment axis and a second rear face inwardly and downwardly inclined with respect to said first rear face.

25. The artificial foot of claim 24, wherein said toes are arranged in a symmetric configuration.

26. The artificial foot of claim 25, wherein said toes comprise a center toe and two outer toes.

27. The artificial foot of claim 24, wherein said foot plate and said ankle plate comprise a vinyl ester resin matrix with a substantially randomly arranged fiberglass fiber content.

28. The artificial foot of claim 24, wherein said ankle plate comprises a through hole in which said bolt resides.

29. The artificial foot of claim 24, wherein said second rear face of said ankle member contacts said upper face of said foot plate at a contact axis to space said contact axis from said heel end of said foot plate by a predetermined amount to provide enhanced plantar flexion.

30. The artificial foot of claim 24, wherein the angle between said first rear face and second rear face of said ankle member is about 60°.

31. The artificial foot of claim 24, wherein the angle between said first rear face and second rear face of said ankle member is between about 45° to about 75°.

32. The artificial foot of claim 24, wherein the angle between said front face of said ankle member and a plane parallel to said first rear face of said ankle member is about 15°.

33. The artificial foot of claim 24, wherein the angle between said front face of said ankle member and a plane parallel to said first rear face of said ankle member is between about 5° to about 45°.

34. The artificial foot of claim 24, further comprising a limit strap generally circumscribing a portion of said posterior section of said ankle member to control the maximum expansion of said posterior section of said ankle member.

35. The artificial foot of claim 34, wherein said limit strap comprises natural tubular nylon webbing.

36. The artificial foot of claim 34, wherein said limit strap comprises woven nylon.

37. A prosthetic foot for providing a smooth and generally life-like response to a wearer, comprising:
  a foot plate comprising a plurality of symmetrically arranged spaced elongated toes;
  an ankle plate positioned above said foot plate;
  a compressible block between said foot plate and said ankle plate and in mechanical communication with said foot plate and said ankle plate for transmitting forces imparted thereon by said foot plate and said ankle plate such that the is a smooth and natural rollover between heel-strike and toe-off as energy is cyclically stored and released in said prosthetic foot; and
  an outer cosmesis housing said foot plate, said ankle plate and said block, said cosmesis comprising a toe region with a slot to form a big toe substantially aligned with one of said toes of said foot plate.

38. The prosthetic foot of claim 37, wherein said foot plate has a generally curvilinear shape.

39. The prosthetic foot of claim 37, wherein said foot plate is capable of flexing along its length.

40. The prosthetic foot of claim 37, wherein said foot plate comprises a middle toe and two outer toes.

41. The prosthetic foot of claim 37, wherein said ankle plate has an anterior section inclined in a direction towards said foot plate.

42. The prosthetic foot of claim 37, wherein said ankle plate is capable of flexing along its length.

43. The prosthetic foot of claim 37, wherein said toe region of said cosmesis comprises a reinforcement patch.

44. The prosthetic foot of claim 43, wherein said reinforcement patch has a slot substantially aligned with said slot of said toe region of said cosmesis.

45. The prosthetic foot of claim 37, wherein said cosmesis has an inner sole that seats said foot plate.

46. The prosthetic foot of claim 37, wherein said cosmesis has an inner slot at said too region that receives said toes of said foot plate.

47. The prosthetic foot of claim 37, where said cosmesis comprises a urethane foam.

48. The prosthetic foot of claim 37, wherein said foam has a molded density of about 25 lb/ft³.

49. The prosthetic foot of claim 37, wherein said block comprises a downwardly and outwardly sloping front face.

50. The prosthetic foot of claim 37, wherein said block comprises a downwardly and inwardly sloping rear surface.

* * * * *

UNITED STATES PATENT AND TRADEMARK OFFICE
CERTIFICATE OF CORRECTION

PATENT NO. : 6,811,571 B1  
APPLICATION NO. : 09/586666  
DATED : November 2, 2004  
INVENTOR(S) : Van L. Phillips et al.

Page 1 of 1

It is certified that error appears in the above-identified patent and that said Letters Patent is hereby corrected as shown below:

On The Title Page, Item (75) Inventor:, line 3 after "92067" please add --; Hilary D. Pouchak, 2902 Rancho Pancho, Carlsbad, CA (US) 92009--.

On The Title Page, Item (56) (Other Publications), line 4, please delete "SVF-175" and insert --SVF175--, therefor.

At column 26, line 22 (Approx.), in Claim 1, delete "life like" and insert --life-like--, therefor.
At column 26, line 39, in Claim 5, delete "where" and insert --wherein--, therefor.
At column 26, line 59, in Claim 12, after "of said" delete "blocks" and insert --block--, therefor.
At column 27, line 3, in Claim 18, delete "ha" and insert --has--, therefor.
At column 27, line 34, in Claim 24, delete "hog" and insert --having--, therefor.
At column 28, line 28, in Claim 37, delete "the" and insert --there--, therefor.
At column 28, line 56 (Approx.) in Claim 46, delete "too" and insert --toe--, therefor.
At column 28, line 58 (Approx.) in Claim 47, delete "where" and insert --wherein--, therefor.
At column 28, line 60 (Approx.) in Claim 48, delete "claim 37" and insert --claim 47--, therefor.

Signed and Sealed this

Twenty-seventh Day of November, 2007

JON W. DUDAS  
*Director of the United States Patent and Trademark Office*